United States Patent
Shimizu et al.

(10) Patent No.: US 7,443,058 B2
(45) Date of Patent: Oct. 28, 2008

(54) ACTUATOR CAPABLE OF RECIPROCAL LINEAR DRIVING AND ROLLING DRIVING AND POWER TOOTHBRUSH USING THE SAME

(75) Inventors: Hiroaki Shimizu, Hikone (JP); Ryo Motohashi, Hikone (JP); Hidekazu Yabuuchi, Hikone (JP); Takahiro Nishinaka, Omihachiman (JP); Katsuhiro Hirata, Sanda (JP); Yuya Hasegawa, Kyoto (JP)

(73) Assignee: Matsushita Electric Works, Ltd., Osaka (JP)

( * ) Notice: Subject to any disclaimer, the term of this patent is extended or adjusted under 35 U.S.C. 154(b) by 122 days.

(21) Appl. No.: 10/557,252

(22) PCT Filed: May 14, 2004

(86) PCT No.: PCT/JP2004/006558

§ 371 (c)(1),
(2), (4) Date: Feb. 5, 2007

(87) PCT Pub. No.: WO2004/102777

PCT Pub. Date: Nov. 25, 2004

(65) Prior Publication Data

US 2007/0145832 A1 Jun. 28, 2007

(30) Foreign Application Priority Data

May 16, 2003 (JP) ............................. 2003-139573

(51) Int. Cl.
*H20K 41/00* (2006.01)

(52) U.S. Cl. ...................... 310/12; 310/13; 310/47; 310/50; 310/80; 310/84; 310/75 A; 310/181

(58) Field of Classification Search .................. 310/12, 310/13, 47, 50, 80, 84, 75 A, 181
See application file for complete search history.

(56) References Cited

U.S. PATENT DOCUMENTS 6,140,723 A * 10/2000 Matsui et al. ................ 310/81

(Continued)

FOREIGN PATENT DOCUMENTS

JP 62-104468 5/1987

(Continued)

OTHER PUBLICATIONS

English language Abstract of JP-9-17336, 1997.

(Continued)

*Primary Examiner*—Iraj A. Mohandesi
(74) *Attorney, Agent, or Firm*—Greenblum & Bernstein, P.L.C.

(57) ABSTRACT

A reciprocal linear driving unit and a rolling driving unit are adjacently provided on a common single shaft in axial direction thereof, so that the reciprocal linear driving in the axial direction and the rolling driving around the axis are performed by the single shaft, simultaneously. Permanent magnets constituting the reciprocal linear driving unit and the rolling driving unit are respectively provided on moving object side instead of stator, in other words, they are provided around the axis of the shaft, thereby respective permanent magnets can be miniaturized and light-weighted. Following to this, miniaturization, light-weighting and cost reduction of an actuator and a power toothbrush using the same can be realized.

13 Claims, 15 Drawing Sheets

U.S. PATENT DOCUMENTS

| | | | |
|---|---|---|---|
| 6,883,199 B1 * | 4/2005 | Lundell et al. | 15/22.1 |
| 7,122,921 B2 * | 10/2006 | Hall et al. | 310/50 |
| 2005/0235438 A1 | 10/2005 | Motohashi et al. | |
| 2006/0010622 A1 | 1/2006 | Naruse et al. | |

FOREIGN PATENT DOCUMENTS

| | | |
|---|---|---|
| JP | 4-75475 | 3/1992 |
| JP | 9-173360 | 7/1997 |
| JP | 2002-176758 | 6/2002 |
| JP | 2002-218727 | 8/2002 |

OTHER PUBLICATIONS

English language Abstract of JP2002-176758, 2002.
English language Abstract of JP 4-075457, 1992.
English language Abstract of JP 62-104468, 1987.
English language Abstract of JP 2002-218727, 2002.
U.S. Appl. No. 10/557,055 to Shimizu et al., which was filed on Nov. 16, 2005.
U.S. Appl. No. 10/557,253 to Shimizu et al., which was filed on Nov. 16, 2005.

* cited by examiner

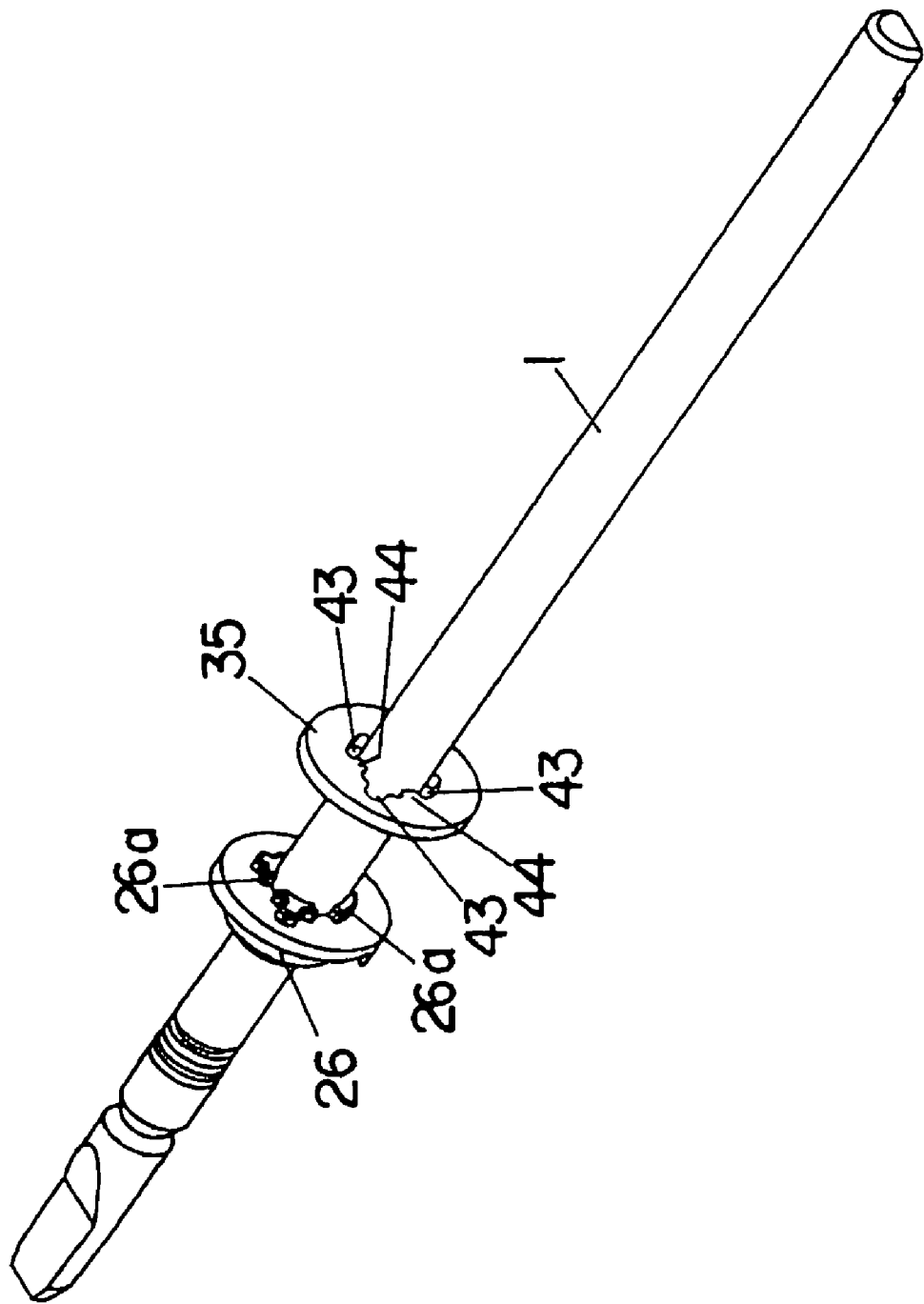

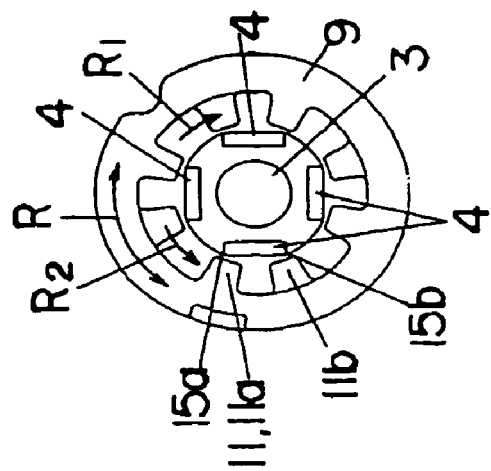
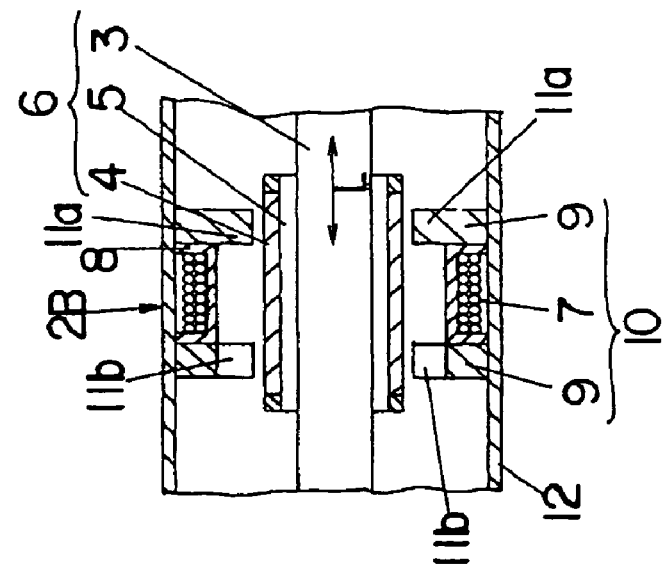
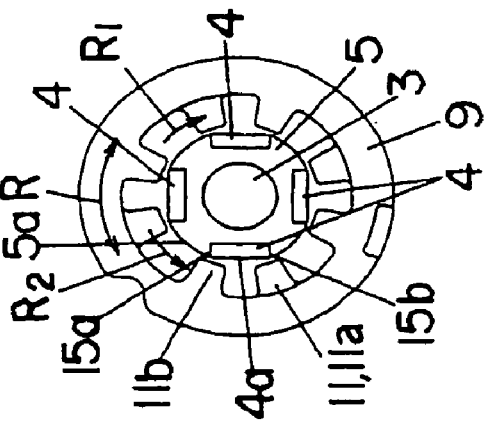
FIG. 8C
FIG. 8A
FIG. 8B

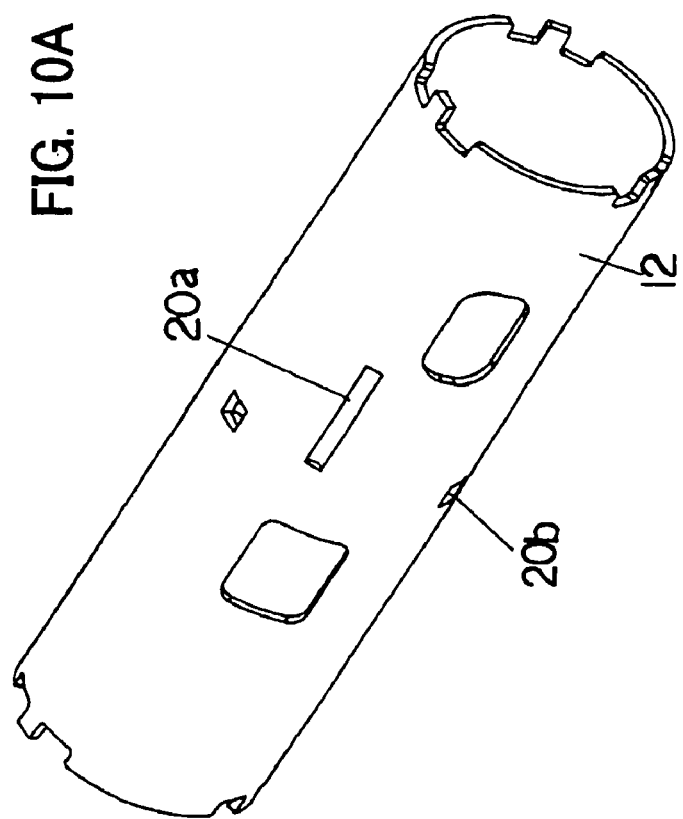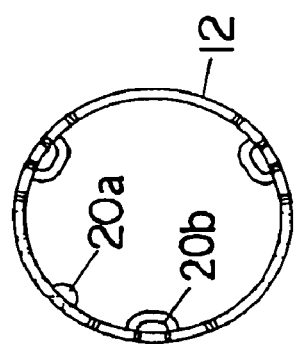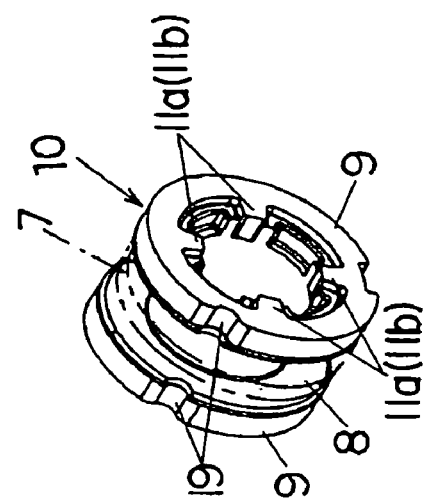
FIG. 10A
FIG. 10B

ACTUATOR CAPABLE OF RECIPROCAL LINEAR DRIVING AND ROLLING DRIVING AND POWER TOOTHBRUSH USING THE SAME

TECHNICAL FIELD

The present invention relates to an actuator capable of reciprocal linear driving of a drive shaft in axial direction thereof and capable of reciprocal rotation driving (rolling driving) around the axis in a predetermined region and a power toothbrush using the same.

BACKGROUND ART

As shown in, for example, Japanese Laid-Open Patent Application No. 9-173360, a power toothbrush, which can perform reciprocal linear driving in axial direction of a shaft and reciprocal rotation driving (rolling driving) around the axis selectively with using mechanical driving conversion mechanism, is known. In this power toothbrush, it is possible selectively to perform two motions of the reciprocal linear driving in the axial direction of the shaft and the rolling driving around the axis of the brush body attached to the shaft via the driving conversion mechanism by switching rotation direction of a motor.

In such a power toothbrush utilizing the mechanical driving conversion mechanism, a configuration of the driving conversion mechanism for switching between the reciprocal linear driving in the axial direction of the shaft and the rolling driving around the axis becomes complex. According to this, the power toothbrush becomes upsizing, and assembly of it becomes difficult causing the increase of the cost. Furthermore, since the reciprocal linear driving in the axial direction and the rolling driving around the axis of the shaft are performed selectively by switching the rotation direction of the motor that is a single actuator, it is impossible to perform the rolling driving of the shaft around the axis simultaneously while performing the reciprocal linear driving in the axial direction.

On the other hand, for example, Japanese Laid-Open Patent Publication No. 2002-176758 shows a power toothbrush which reciprocally and linearly drives a brush body attached on a shaft in axial direction of the shaft with using a reciprocation type linear driving actuator. This reciprocation type linear driving actuator can perform only the reciprocal linear driving of the shaft, but cannot perform the rolling driving. It, however, is described as a reference of the conventional actuator using permanent magnets and coil.

This conventional actuator is described with reference to FIG. 15. With this conventional reciprocation type linear driving actuator 150, a plunger 151 formed of a magnetic material is fixed on an outer periphery of a shaft 152. The shaft 152 is pivoted by a bearing 162 capable of reciprocally and linearly moving in a direction (axial direction) parallel to the center axis thereof. A ring shaped coil 154 is disposed on an inner peripheral surface of a shielding case 153 with a predetermined clearance with respect to the outer periphery of the plunger 151. Furthermore, ring shaped permanent magnets 155 and 156 which are magnetized in symmetrical with respect to the coil 154 are disposed on the inner peripheral surface of the shielding case 153 and on both sides of the coil 154 in the above axial direction. Ring shaped first yokes 157 and 158 are respectively disposed between the permanent magnets 155 and 156 and the coil 154, and ring shaped second yokes 159 and 160 are disposed at positions opposite to the permanent magnets 155 and 156 with respect to the coil 154. A spring member 161 is disposed between the plunger 151 and the shielding case 152 (SIC: correctly 153) for applying an accompanying force to the plunger 151 in a one direction among the reciprocation directions of linear driving. Then, by supplying an alternating current to the coil 154, the plunger 151 can be reciprocally and linearly driven in the axial direction.

However, in the above-mentioned reciprocation type linear drive actuator 150 using the conventional permanent magnets and the coil, the permanent magnets 155 and 156 are disposed with the clearance with respect to the outer periphery of the plunger, so that inside diameter and outside diameter of the ring shaped permanent magnets 155 and 156 become larger, and volumes of the permanent magnets 155 and 156 also become larger. Following to this, the cost of the permanent magnets 155 and 156 in material becomes expensive. Furthermore, since the permanent magnets 155 and 156 are formed as the ring shape by combination of a plurality of arc-shaped permanent magnets, manufacturing process of the ring shaped permanent magnets 155 and 156 becomes complicated, and the cost of them in manufacturing becomes expensive. As a result, the costs of the actuator using the conventional permanent magnets and coil and the power toothbrush using the same become expensive. Still furthermore, since the permanent magnets 155 and 156 are larger, it is difficult to realize the miniaturization and weight saving of the actuator 150 and the power toothbrush using the same.

DISCLOSURE OF INVENTION

The present invention is done to solve the problems of the above-mentioned conventional ones and purposed to provide an actuator capable of reciprocal linear driving and rolling driving of a shaft enabling low cost, miniaturization, weight saving and improvement of assemble workability, and to provide a power toothbrush using the same with low cost, miniaturization and weight saving.

For achieving the above mentioned purpose, an actuator capable of reciprocal linear driving and rolling driving in accordance with an aspect of the present invention comprises a reciprocal linear driving unit and a rolling driving unit which are arranged to adjoin in axial direction of a shaft. The shaft is pivoted to be enabled reciprocal linear driving in the axial direction thereof and pivoted to be enabled rolling driving around the axis of the shaft in a predetermined region.

The reciprocal linear driving unit comprises: a first moving object having the shaft and first permanent magnets each magnetized so that polarities of both end portions in the axial direction of the shaft are different and fitted to and fixed on the shaft; and a first stator having a coil disposed to face end faces of the first permanent magnets parallel to the axial direction of the shaft with a predetermined clearance and generating magnetic field when current is supplied.

The rolling driving unit comprises:
a second moving object having the shaft, a second yoke fixed on the shaft and at least one second permanent magnet attached to adjoin the second yoke around the axis of the shaft; and a tubular shaped second stator having a second coil wound around the axis of the shaft to enclose the second moving object, and second stationary yokes disposed to face an outermost peripheral portion of the yoke (SIC: correctly second yoke) and the second permanent magnet with a predetermined clearance in a direction perpendicular to the axis of the shaft.

Then, by supplying an alternating current to the first coil and/or the second coil, the first moving object is driven reciprocally and linearly in the axial direction of the shaft and/or the second moving object is driven rollingly around the axis of the shaft in a predetermined angle region.

According to such a configuration, the reciprocal linear driving unit and the rolling driving unit are provided on a single common shaft to adjoin in the axial direction thereof, so that reciprocal linear motion and rolling driving can be performed by the single shaft, simultaneously. Furthermore, the permanent magnets which constitute the reciprocal linear driving unit and the rolling driving unit are respectively provided on not the stator side but the moving object side, that is, around the axis of the shaft, so that the permanent magnets can be miniaturized and light-weighted respectively, in comparison with the case that the permanent magnets with larger diameter are provided on the stator side like the conventional one. Following to this, it is possible further to realize miniaturization, light-weighting and cost reduction of the actuator.

On the other hand, a power toothbrush using an actuator enabling reciprocal linear driving and rolling driving in accordance with an aspect of the present invention comprises: a brush body that brush is implanted at a front end thereof; an actuator which can perform reciprocal linear driving and rolling driving of the brush body in predetermined directions; an electric power supply for supplying electric power to the actuator; a driving circuit for supplying driving current to the actuator; and an electric switch for switching driving mode of the actuator corresponding to operation by a user.

The actuator comprises a reciprocal linear driving unit and a rolling driving unit which are arranged to adjoin in axial direction of a shaft. The shaft is pivoted to be enabled reciprocal linear driving in the axial direction thereof and pivoted to be enabled rolling driving around the axis of the shaft in a predetermined region.

The reciprocal linear driving unit comprises: a first moving object having the shaft and first permanent magnets each magnetized so that polarities of both end portions in the axial direction of the shaft are different and fitted to and fixed on the shaft; and a first stator having a coil disposed to face end faces of the first permanent magnets parallel to the axial direction of the shaft with a predetermined clearance and generating magnetic field when current is supplied.

The rolling driving unit comprises: a second moving object having the shaft, a second yoke fixed on the shaft and at least one second permanent magnet attached to adjoin the second yoke around the axis of the shaft; and a tubular shaped second stator having a second coil wound around the axis of the shaft to enclose the second moving object, and second stationary yokes disposed to face an outermost peripheral portion of the yoke (SIC: correctly second yoke) and the second permanent magnet with a predetermined clearance in a direction perpendicular to the axis of the shaft.

The electric switch switches among a mode for driving only the first moving object reciprocally and linearly in the axial direction of the shaft, a mode for driving only the second moving object rollingly around the axis of the shaft in a predetermined angle region, and a mode for driving the first moving object reciprocally and linearly in the axial direction of the shaft and driving the second moving object rollingly around the axis of the shaft in a predetermined angle region simultaneously.

According to such a configuration, the brush body attached to the front end of the shaft can be driven in one of the mode for driving it reciprocally and linearly in the axial direction of the shaft, the mode for driving it rollingly around the axis, and the mode for driving it reciprocally and linearly in the axial direction of the shaft and rollingly around the axis simultaneously. Furthermore, the miniaturization, light-weighting and cost reduction of the actuator are possible as mentioned above, so that the miniaturization, light-weighting and cost reduction of the power toothbrush using the same can be realized, too.

BRIEF DESCRIPTION OF DRAWINGS

FIG. 6 is a perspective view showing a state that a spring receiving member and the above first yoke are coupled in the above modified example.

FIG. 8A is a sectional side view showing a configuration of an opposing portion of the above second moving object and a second stator of the above actuator. FIG. 8B is a rear view showing the configuration of the opposing portion of the above second moving object and the second stator. FIG. 8C is a front view showing the configuration of the opposing portion of the above second moving object and the second stator.

FIG. 10A is an exploded perspective view showing a configuration of a shielding case and the second stator in the above actuator. FIG. 10B is a sectional front view showing the configuration of the shielding case.

BEST MODE FOR CARRYING OUT THE INVENTION

An actuator capable of reciprocal linear driving and rolling driving and a power toothbrush using the same in accordance with an embodiment of the present invention is described in detail with reference to drawings.

Figure 1:
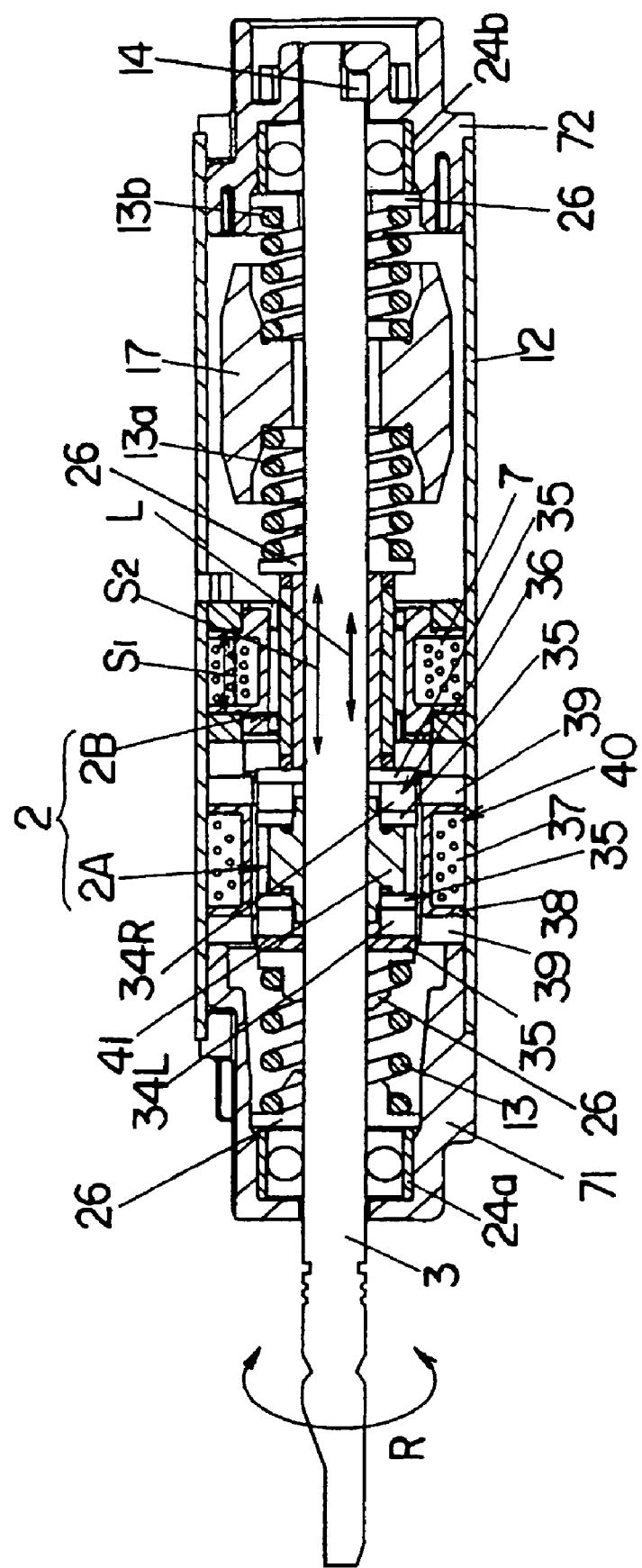
FIG. 1 is a sectional side view showing a configuration of an actuator capable of reciprocal linear driving and rolling driving in accordance with an embodiment of the present invention.
Figure 2A:
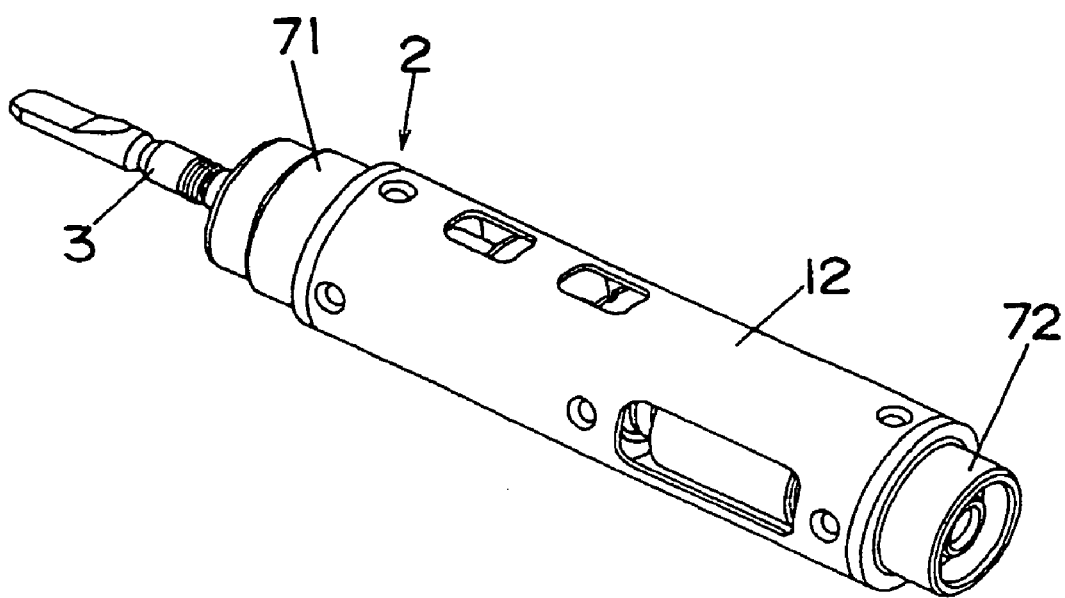
FIG. 2A is a perspective view showing an outer appearance configuration of the actuator shown in FIG. 1.
Figure 2B:
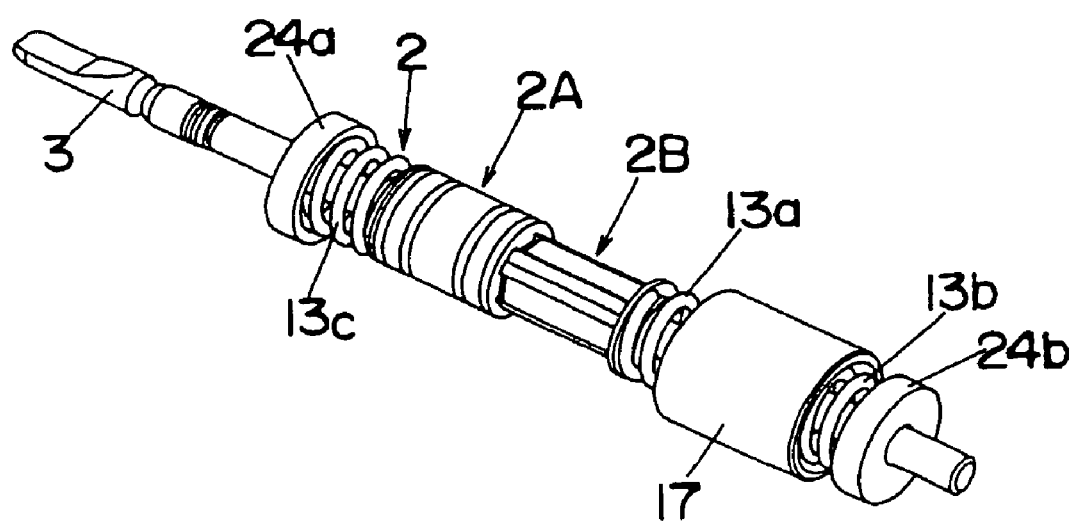
FIG. 2B is a perspective view showing an inner configuration in a state that a shielding case is detached.
Figure 3:
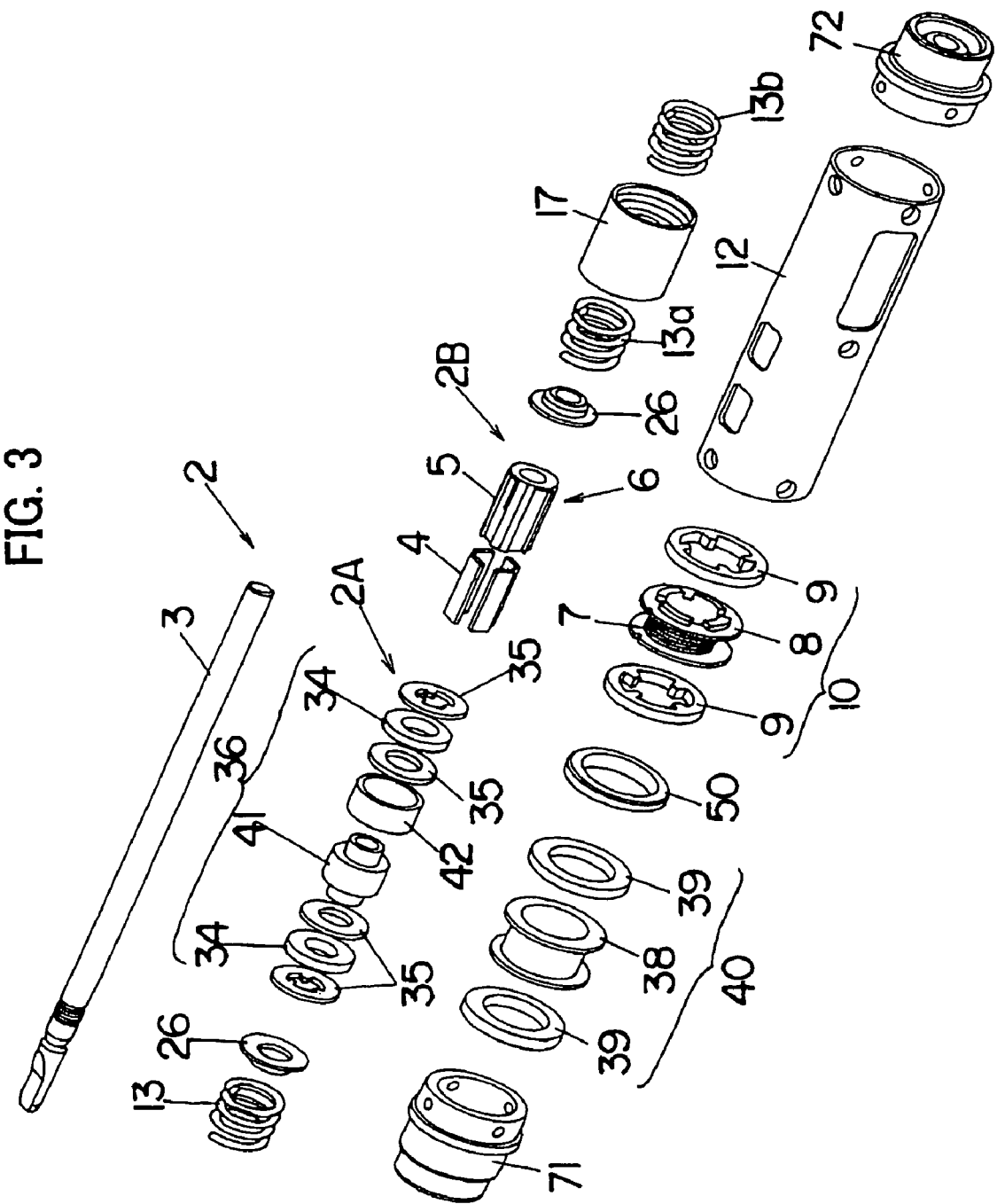
FIG. 3 is an exploded perspective view of the actuator shown in FIG. 1.
Figure 4:
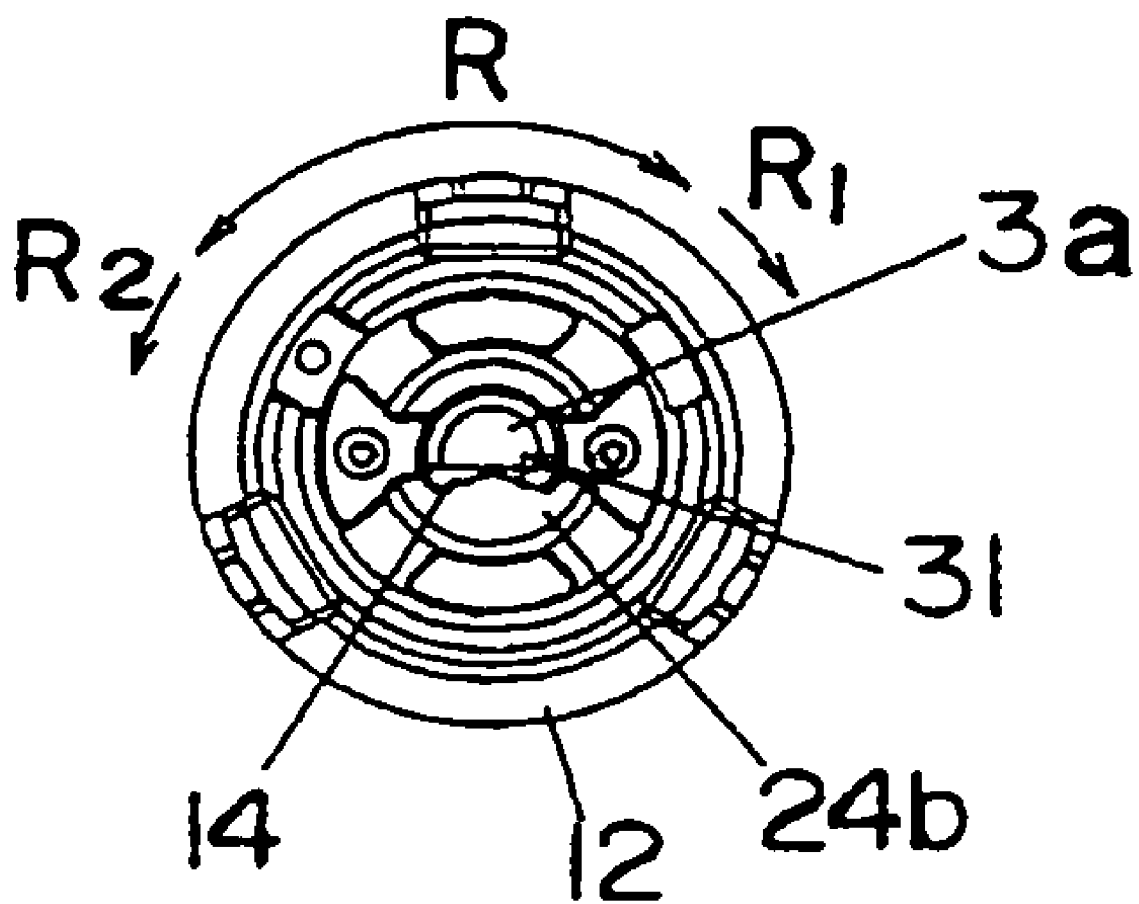
FIG. 4 is a view showing a structure for restricting rotation angle of a shaft provided at a rear end portion of the actuator shown in FIG. 1.

First, an actuator capable of reciprocal linear driving and rolling driving in accordance with this embodiment which is suitable for an actuator of a power toothbrush is described. FIG. 1 is a sectional side view showing a configuration of the actuator 2 capable of reciprocal linear driving and rolling driving in accordance with this embodiment. FIG. 2A is a perspective view showing an outer appearance configuration of the actuator 2. FIG. 2B is a perspective view showing an inner configuration in a state that a shielding case is detached. FIG. 3 is an exploded perspective view of the actuator 2. FIG. 4 is a view showing a structure for restricting rotation angle of a shaft provided at a rear end portion of the actuator 2.

The actuator 2 comprises a reciprocal linear driving unit 2A for driving a shaft 3 reciprocally and linearly in axial direction thereof, and a rolling driving unit 2B for driving the shaft 3 reciprocally and rotationally around an axis thereof in a predetermined region (rolling driving).

A shielding case 12 is a substantially tubular shape, and sealing members 71 and 72 are respectively fitted and fixed to openings at front and rear ends thereof. Furthermore, bearings 24a and 24b for pivoting the shaft 3 reciprocally and linearly in the axial direction thereof as shown by arrow L and reciprocally and rotatably around the axis thereof in a predetermined region as shown by arrow R are respectively provided on the sealing members 71 and 72. Then, the reciprocal linear driving unit 2A for performing the shaft 3 in reciprocal linear driving in the axial direction thereof and the rolling driving unit 2B for driving the shaft 3 rollingly around the axis thereof are provided in an inside of the shielding case 12.

The reciprocal linear driving unit 2A for performing the shaft 3 in the reciprocal linear driving in the axial direction shown by arrow L is described first. The reciprocal linear driving unit 2A comprises a first moving object 36 and a tubular shaped first stator 40.

The first stator 40 is formed of substantially cylindrical shape, and disposed on an inner peripheral surface of the shielding case 12. The first stator 40 is configured by a first coil 37 formed by winding a wire around a first bobbin 38, and first stationary yokes 39 of substantially ring shape provided at both sides of the first bobbin 38.

The first moving object 36 is configured by the shaft 3, first permanent magnets 34, first yokes 35, a spacer 41, an iron core 42, and so on. Generally, if the shaft 3 is made of a nonmagnetic material, no magnetic flux leaks through the shaft 3, so that power loss can be reduced. However, the nonmagnetic material is generally expensive. And, strength of inexpensive nonmagnetic material is lower. Thus, in this embodiment, the shaft 3 is made of a magnetic material for maintaining strength of the shaft 3 and for reducing the cost. Then, the spacer 41 is fitted to and fixed on the shaft 3, and furthermore, circular or tubular shaped two first permanent magnets 34 which are disposed with a predetermined distance and circular or tubular shaped four yokes which are disposed to adjoin both end faces of the first permanent magnets 34 are fitted to and fixed on the shaft 3 via the spacer 41. Still furthermore, the iron core 42 is fitted to and fixed on an outer peripheral face of the spacer 41.

Besides, as shown in the figures, a thickness, that is, a length in the axial direction of the shaft 3 of the first permanent magnets 34 is shorter than a dimension of the first permanent magnets 34 in a direction perpendicular to the axis of the shaft 3, so that it will be called "ring shape" in the following description. However, the first permanent magnets 34 used in the actuator in accordance with the present invention are not limited to the ring shape and may be tubular shape that the length in the axial direction of the shaft 3 is substantially equal to or longer than the dimension in the direction perpendicular to the axis of the shaft 3.

The first permanent magnets 34 are respectively magnetized in thickness direction, so that polarities at both end face portions in the axial direction of the shaft 3 are set to be different from each other. Furthermore, two first permanent magnets 34 are fixed on the shaft 3 in a manner so that polarities of the faces facing each other become the same. For example, when the polarity at the left end face of the first permanent magnet 34 at left side is assumed as S-pole, the polarity at the right end face of the first permanent magnet 34 becomes N-pole, the polarity at the left end face of the first permanent magnet 34 at right side becomes N-pole, and the polarity at the right end face of the first permanent magnet 34 becomes S-pole, and vice versa. In this way, it is possible to generate larger magnetic flux by arranging two first permanent magnets 34 on the shaft 3 in parallel with the axial direction thereof.

The first moving object 36 configured that the first permanent magnets 34 are fitted to and fixed on the shaft 3 is inserted into the shielding case 12 in a manner to be distant with a predetermined clearance with respect to the inner peripheral surface of the first stator 40 which is fixed on the shielding case 12. The distance between two first permanent magnets 34 is set to be narrower than a distance between two first stationary yokes 39 of the first stator 40. Furthermore, under a state that the first moving object 36 is not driven in the reciprocal linear driving in the axial direction of the shaft 3 shown by arrow L, it is set that the center position between two first stationary yokes 39 substantially coincides with the center position between two first permanent magnets 34. Besides, it is not necessarily limited to this constitutional example, and the distance between two first permanent magnets 34 may be substantially equal to or wider than the distance between two first stationary yokes 39 of the first stator 40.

Figure 5B:
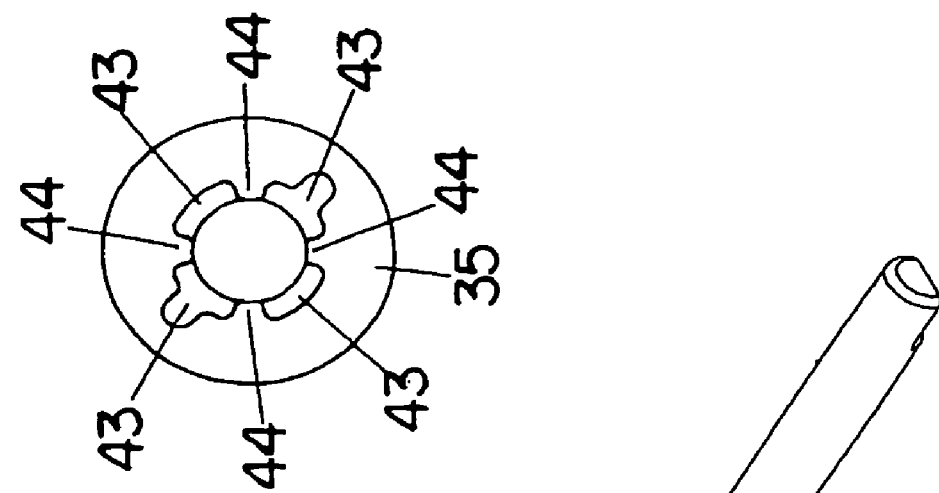
FIG. 5B is a front view showing a shape of the above first yoke.
Figure 5A:
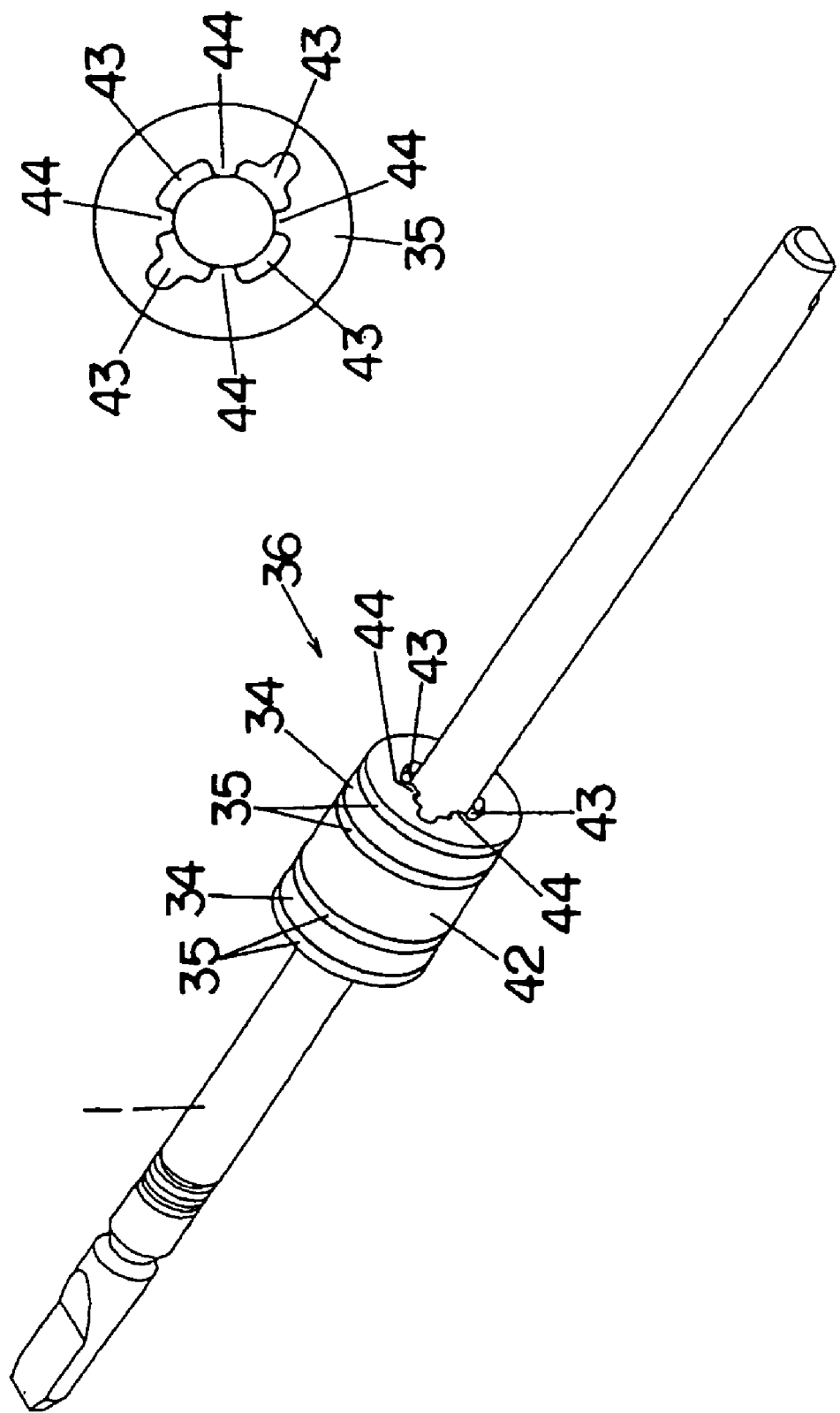
FIG. 5A is a perspective view showing a modified example of a structure for fitting and fixing first permanent magnets and first yokes to and on the shaft which constitute a first moving object in the above embodiment.

Hereupon, a modified example of a structure for fitting and fixing the first permanent magnets 34 and the first yokes 35 to and on the shaft 3 is shown in FIG. 5A and FIG. 5B. In the above mentioned constitutional example, the spacer 41 is fitted to the shaft 3 made of a magnetic material, and furthermore, the first permanent magnets 34 and the first yokes 35 are fixed on the spacer. On the other hand, in the modified example shown in FIG. 5A and FIG. 5B, a plurality of (for example, four) protrusions 44 and gaps 43 between each protrusion 44 are formed on an inner periphery portion of the first yokes 35 instead of the spacer 41, and the first yokes 35 are fitted to and fixed on the shaft 3 by contacting the protrusions 44 on an outer peripheral face of the shaft 3. Although it is not illustrated, the same does for the permanent magnets 34. As a result, regardless of the shaft 3 made of a magnetic material for reduction of cost and maintaining the strength of the shaft 3, magnetic flux by the permanent magnets 34 rarely passes through the shaft 3, and most of it can be passed through the first stationary yokes 39 side, so that the magnetic flux by the permanent magnets 34 can be utilized effectively.

Subsequently, the rolling driving unit 2B for driving the above shaft 3 rollingly around the axis as shown by arrow R is described. The rolling driving unit 2B comprises a second moving object 6 and a tubular shaped second stator 10.

The second moving object 6 is configured by the shaft 3, a second yoke S press-fitted to and fixed on the shaft 3, a flat plate shaped second permanent magnets 4 fixed on the second yoke 5, and so on. The second stator 10 is configured by a second bobbin 8, a second coil 7 constituted by winding a wire around the second bobbin 8, second stationary yokes 9 disposed at both sides of the second bobbin 8 in axial direction of the shaft 3, and so on. The second stator 10 is formed substantially tubular shape, and fixed on the inner peripheral face of the shielding case 12. When the shaft 3 is pivoted by the bearings 24a and 24b, the second moving object 6 is held in a manner so that an outermost peripheral portion of the second moving object 6 in a direction perpendicular to the axis of the shaft 3 keeps a predetermined clearance with respect to an innermost peripheral portion of the second stator 10. In this way, by rotatably inserting the second moving object 6 into the inside of the second stator 10, a magnetic circuit of the actuator 2 for rolling driving is constituted. Besides, the second stationary yokes 9 are not necessarily provided on both sides of the second bobbin 8, and it may be provided on only one side.

As shown in FIG. 1, the second moving object 6 has a length S2 in a reciprocal moving region in the axial direction of the shaft 3 shown by arrow L by which a clearance between the second permanent magnets 4 and magnetic poles 11 of the second stationary yokes 9 can be held constant. Specifically, in the axial direction of the shaft 3, the length S2 of the second permanent magnet 4 is set to be longer than a distance S1 between the second stationary yokes 9 (S1<S2) under a state that the center position of the second permanent magnet 4 of the second moving object 6 substantially coincides with the center position between two second stationary yokes 9 provided on both sides of the second bobbin 8. Thus, the second moving object 6 can be held a constant clearance consistently without departing the second permanent magnets 4 and the magnetic poles 11 of the second stationary yokes 9 in the region where the reciprocal linear driving can be performed in the axial direction of the shaft 3. As a result, the rolling driving of the second moving object 6 around the axis of the shaft 3 shown by arrow R can be performed continuously.

Figure 7:
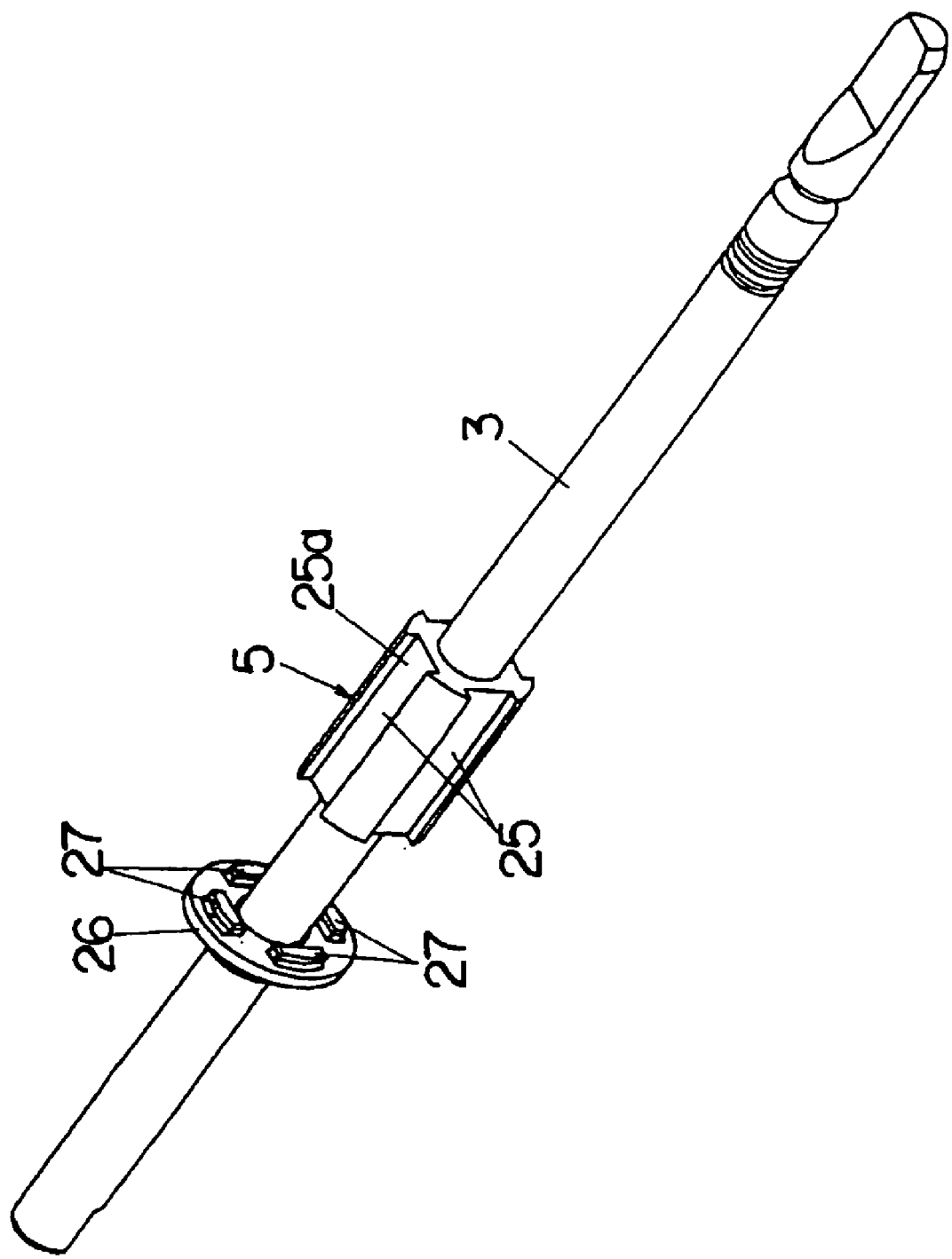
FIG. 7 is a perspective view showing a state that a second yoke and a spring receiving member which constitute a second moving object of the above actuator are assembled on the shaft.

A state that the second yoke 5 is press-fitted to and fixed on the shaft 3 is shown in FIG. 7. Furthermore, a configuration of an opposing portion of the second moving object 6 and the second stator 10, that is, a main portion for generating driving force is shown in FIG. 8A to FIG. 8C. As can be seen from these figures, the second yoke 5 is formed of a magnetic material to be substantially tubular shape, and at least one (four in the figures) of groove 25 is formed on an outer peripheral face. thereof. Each groove 25 is formed along the axis of the shaft 3 to have a substantially U-shaped section (channel shape) so that a bottom face thereof is to be flat. Then, since a depth of the groove 25 and a thickness of the second permanent magnet 4 and a width of the groove 25 and a width of the second permanent magnet 4 are respectively set to be substantially equal, the flat plate shaped second permanent magnets 4 are respectively fitted to the grooves 25 substantially with no clearance, as shown in FIG. 8A to FIG. 8C. As a result, it becomes a state that an outer face 4a of each flat plate shaped second permanent magnet 4 is disposed to adjoining an arc shaped outer face 5a of the second yoke 5.

Each second permanent magnet 4 is magnetized in thickness direction so that a polarity of the outer face 4a and a polarity of an inner face 4b in a direction perpendicular to the axis of the shaft 3 are different from each other. Furthermore, each second permanent magnet 4 is fixed on the second yoke 5 in the same orientation that, for example, all of the outer faces 4a of four second permanent magnets 4 become N-pole. By fixing the second permanent magnets 4 on the second yoke 5 in this way, all arc shaped outer faces 5a of the second yoke 5 disposed between two adjoining second permanent magnets 4 become S-pole, and vice versa.

FIGS. 8A to 8C respectively show an initial state that no current is supplied to the second coil 7. When no current is supplied to the second coil 7, the second moving object 6 is stopped at a position where the magnetic force of the second permanent magnets 4 applied to the second stationary yokes 9 and forces of spring members 13a, 13b and 13c are balanced. Then, magnetic poles 11a and 11b provided on the second stationary yokes 9 are respectively positioned to face the second permanent magnets 4. When a unidirectional current is supplied to the second coil 7, the magnetic poles 11a of one second stationary yoke 9 become N-pole, and the magnetic poles 11b of the other second stationary yoke 9 become S-pole. Thus, as shown in FIG. 4, the second moving object 6 rotates in a direction around the axis of the shaft 3, for example, in the direction shown by arrow R1. When a reverse current is supplied to the second coil 7, the magnetic poles 11a of one second stationary yoke 9 become S-pole, and the magnetic poles 11b of the other second stationary yoke 9 become N-pole. Thus, the second moving object 6 rotates in the other direction around the axis of the shaft 3, for example, in the direction shown by arrow R2. Accordingly, by supplying an alternating current to the second coil 7, it is possible to perform the rolling driving of the second moving object 6 in a predetermined angle region around the axis of the shaft 3 as shown by arrow R.

Spring receiving members 26 made of nonmagnetic material are respectively fitted to the shaft 3 for facing a rear face of the bearing 24a at front side, a front end face of the first moving object 36, a rear end face of the second moving object and a front face of the bearing 24b at rear side. Furthermore, the substantially tubular shaped vibrational absorption spindle 17 is inserted between the second moving object 6 and the bearing 24b at rear side with a relatively large tolerance with respect to the shaft 3. Then, coil springs 13a and 13b are respectively provided between the spring receiving members 26 and the vibrational absorption spindle 17, and a coil spring 13c is provided between the spring receiving members 26 of the first moving object 36 and the bearing 24a at front side.

Figure 11:
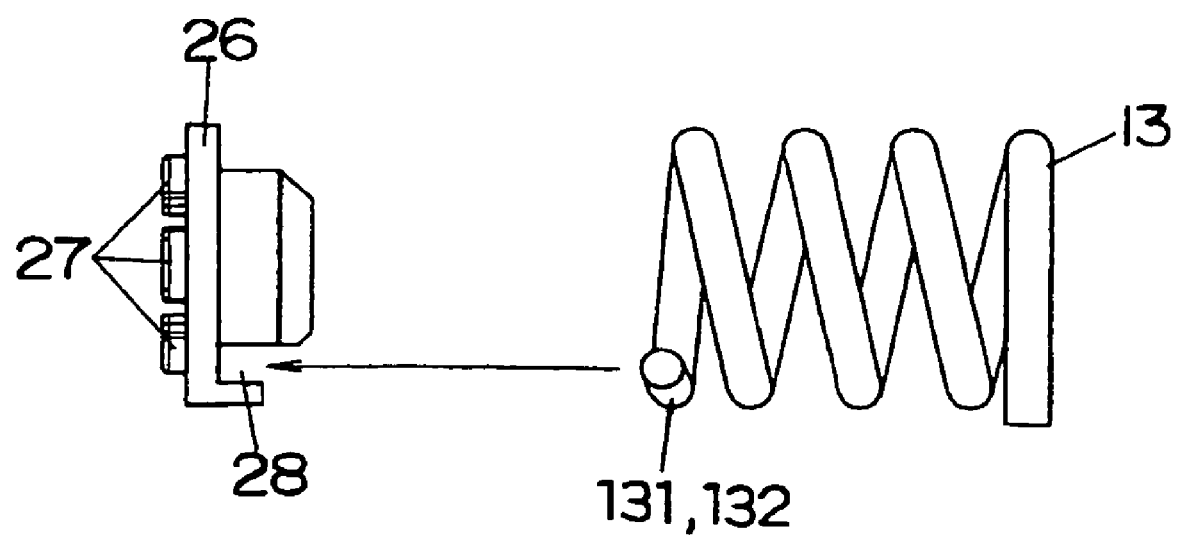
FIG. 11 is a side view showing a state that an end of a spring member is engaged with the above spring receiving member.
Figure 12C:
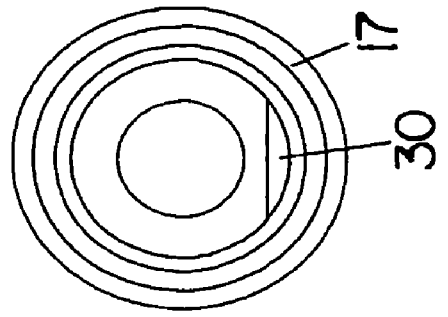
FIGS. 12A to 12D are respectively front view, a sectional side view, a rear view and a perspective view showing a configuration of a vibrational absorption spindle of the above actuator.
Figure 12D:
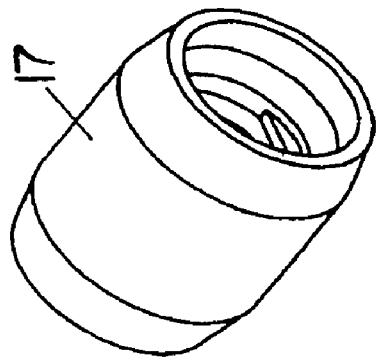
Figure 12B:
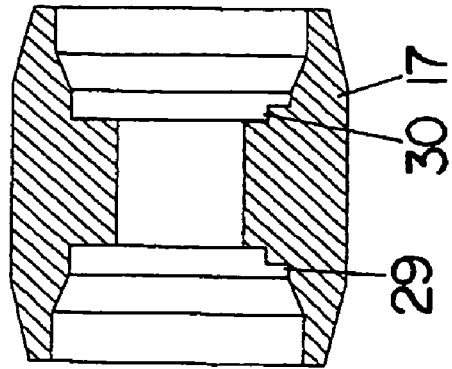
Figure 12A:
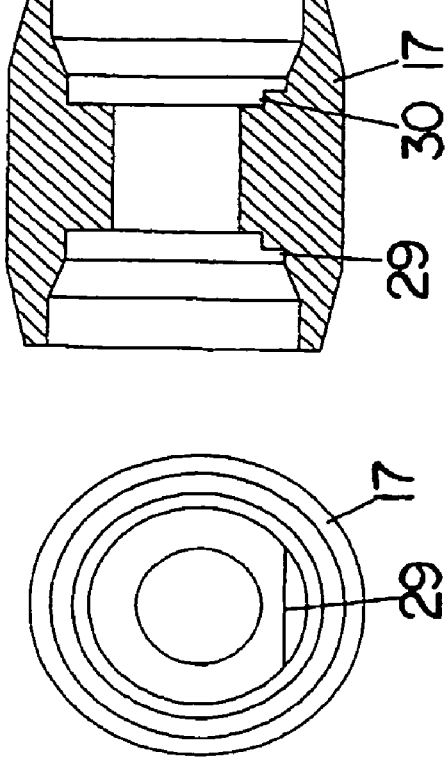

Configurations of the spring members 13a, 13b and 13c and the spring receiving members 26 are shown in FIG. 11. The spring members 13a, 13b and 13c are substantially the same shape, and each constituted by a torsion coil spring 13 having two arms 131 and 132. A hooking portion 28 is formed on each spring receiving member 26 to nip the arm 131 or 132 of the spring members 13a, 13b and 13c for restricting rotation of the spring members 13a, 13b and 13c.

Two among four spring receiving members 26 are fixed on the bearings 24a and 24b of the shielding case 12 so as not to rotate around the axis of the shaft 3, so that it is not movable with respect to the first stator 40 and the second stator 10. The remaining two spring receiving members 26 are fixed on the first moving object 36 and the second moving object 6 which rotate around the axis of the shaft 3, so that they displace with the first moving object 36 and the second moving object 6. Thus, the springs 13a, 13b and 13c are respectively rotated in tightening direction or loosening direction when the second moving object 6 is rotated around the axis of the shaft 3, so that elastic reaction forces are charged in the springs 13a, 13b and 13c. As a result, the rotatable region around the axis of the shaft 3 is restricted.

Furthermore, a configuration of the vibrational absorption spindle 17 is shown in FIGS. 12A to 12D. Hooking portions 29 and 30 are formed on the vibrational absorption spindle 17 too, for preventing the rotation by hooking the arm 131 or 132 of the spring members 13a and 13b. In this way, since respective arms 131 and 132 of three spring members 13a, 13b and 13c are fixed for stopping the rotation by the hooking portions 28, 29 and 30 of the spring receiving members 26 and the vibrational absorption spindle 17, the first moving object 36 is held in a state of reciprocally and linearly movable in the axial direction of the shaft 3 shown by arrow L, and the second moving object 6 is held in a state of rotatable around the axis of the shaft 3 shown by arrow R. Since the position of the center of gravity of the vibrational absorption spindle 17 is disposed on the same axis as the rotation axis of the second moving object 6, the second moving object 6 and the vibrational absorption spindle 17 are respectively driven in rotation in opposite phases when the second moving object 6 is rotated around the axis of the shaft 3.

In the actuator 2 in accordance with this embodiment, it is possible to drive the shaft 3 reciprocally and linearly in the axial direction thereof or rollingly around the axis thereof by applying an alternating current to the first coil 37 and the second coil (SIC: numeric reference 7 is missed), selectively. Furthermore, it is possible to drive the shaft 3 reciprocally and linearly in the axial direction thereof and rollingly around the axis thereof simultaneously by applying alternating currents to the first coil 37 and the second coil (SIC), simultaneously.

In case of performing the shaft 3 in reciprocal linear driving in the axial direction shown by arrow L, a vibration system of reciprocal linear motion of the first moving object 36 is constituted by the first moving object 36 and the spring members 13a, 13b and 13c. In other words, three spring members 13a, 13b and 13c are extended and compressed corresponding to the reciprocal linear motion of the first moving object 36, so that compression force and extension force are applied to the first moving object 36.

In a state that no current flows in the first coil 37, the first moving object 36 is stopped at a position where magnetic force of the first permanent magnets 34 applied to the first stationary yokes 39 is balanced with charging force of the spring members 13a, 13b and 13c, and outer side faces of two first permanent magnets 34 of the first moving object 36 respectively face inner side faces of the first stationary yokes 39.

When a unidirectional current flows in the first coil 37, the first moving object 36 moves to a direction, and when a reverse current flows in the first coil 37, the first moving object 36 moves to the reverse direction. Thus, by giving an alternating current flow in the first coil 37, the first moving object 36 can be driven reciprocally and linearly in the axial direction of the shaft 3. Especially, by flowing an alternating current near to resonance frequency defined by spring constant of the spring members 13a, 13b and 13c and masses of the first moving object 36 and the second moving object 6 in the first coil 37, the reciprocal linear driving (reciprocal oscillation) of the first moving object 36 can be made in a state near to resonance oscillation state, thereby the moving quantity (quantity of amplitude) of the first moving object 36 can be enlarged.

On the other hand, in case of performing the shaft 3 in reciprocal rotation driving around the axis thereof shown by arrow R, a vibration system of the rolling driving of the second moving object 6 is constituted by the second moving object 6 and the spring members 13a, 13b and 13c. In other words, the spring members 13a, 13b and 13c are tortured in tightening direction and in loosening direction corresponding to the rolling driving of the second moving object 6 around the axis of the shaft 3. As a result, it applies a charging force in a direction for restricting the rotation of the second moving object 6 around the axis of the shaft 3. By applying a current having a frequency near to a resonance vibration frequency defined by a spring constant of the spring members 13a, 13b and 13c and masses of the first moving object 36 and the second moving object 6 to the second coil 7, oscillation quantity (amplitude quantity) of the second moving object 6 can be enlarged.

When a unidirectional current is supplied to the second coil 7, the second permanent magnet 4 receives magnetic repulsion force from the magnetic pole 11a of one second stationary yoke 9 and simultaneously receives magnetic attraction force from the magnetic pole 11b of the other second stationary yoke 9. Thus, the second moving object 6 is rotatively driven in a direction around the axis of the shaft 3 (for, example, in a direction shown by arrow R1) with a large force. When a reverse current is supplied to the second coil 7, the second permanent magnet 4 receives magnetic attraction force from the magnetic pole 11a of one second stationary yoke 9 and simultaneously receives magnetic repulsion force from the magnetic pole 11b of the other second stationary yoke 9, so that the second moving object 6 is rotatively driven in the other direction around the axis of the shaft 3 (for, example, in a direction shown by arrow R2) with a large force. Therefore, by supplying an alternating current to the second coil 7, the rolling driving of the second moving object 6 around the axis of the shaft 3 can be performed.

Furthermore, the outer face 4a of the second permanent magnet 4 and the outer face 5a of the second yoke 5, polarities of which are different from each other, are disposed to adjoin each other in a peripheral direction of the second moving object 6, so that driving force for rotating the second moving object 6 is generated between the magnetic poles 11a and 11b and the outer face 5s of the second yoke 5. Still furthermore, the outer face 4a of the second permanent magnet 4 is flat, so that an opposing area of it with respect to the magnetic pole 11 can be ensured largely. On the other hand, the outer face 5a of the second yoke 5 is arc shape, so that a clearance between the magnetic pole 11 and it can be reduced with ensuring an opposing area of it with respect to the magnetic pole 11. Thus, the driving force for rotating the second moving object 6 around the axis of the shaft 3 is further increased, and the driving force in an initial state of rotation of the second moving object 6 becomes larger, so that the rolling driving can be started smoothly.

When the first stator 40, the second stator 10 and the shielding case 12 are assumed as stationary portion, it can be handled as a system of two mass point vibration model of gross mass of the first moving object 36 and the second moving object 6 and mass of the vibrational absorption spindle 17. The vibrational absorption spindle 17 is commonly used for the vibration system of the reciprocal linear driving and the vibration system of the rolling driving. When the reciprocal linear driving by the first moving object 36 and the rolling driving by the second moving object 6 are simultaneously performed, the vibrational absorption spindle 17 is reciprocally and linearly driven in the axial direction of the shaft 3 in opposite phase to that of the first moving object 36, and rotatively driven around the axis of the shaft 3 in opposite phase to that of the second moving object 6. In this case, there are the first (low-order side) oscillation mode that the first moving object 36 or the second moving object 6 and the vibrational absorption spindle 17 are driven in the same phase and the second (high-order side) oscillation mode that the first moving object 36 or the second moving object 6 and the vibrational absorption spindle 17 are driven in opposite phase. When the first moving object 36 is driven reciprocally and linearly in the axial direction or when the second moving object 6 is driven rollingly around the axis by supplying a current having a frequency near to natural vibration frequency in the second vibration mode to the first coil 37 or the second coil 7, the vibrational absorption spindle 17 which is driven in opposite phase cancels inertial force of the first moving object 36 and the second moving object 6, and in reverse, the first moving object 36 and the second moving object 6 cancel inertial force of the vibrational absorption spindle 17. Thereby, the vibration propagated to the shielding case 12 can be reduced. Still furthermore, a gap 18 is provided between the vibrational absorption spindle 17 and the shaft 3 in a direction perpendicular to the axis of the shaft 3. The gap 18 is an air gap and serves to rotate the vibrational absorption spindle 17 around the axis of the shaft 3 with smooth motion and with no resistance. Although, it is possible to intervene a bearing or the like, it is preferable to provide the gap 18 for restricting the cost lower.

Furthermore, moment of inertia of the vibrational absorption spindle 17 is set to be larger than moment of inertia of the first moving object 36 and the second moving object 6 in rotation of the second moving object 6. In this embodiment, the moment of inertia of the vibrational absorption spindle 17 may be made larger than the moment of inertia of the first moving object 36 and the second moving object 6 by adjusting the weight of the vibrational absorption spindle 17. By increasing the moment of inertia of the vibrational absorption spindle 17, assisting force of the rotation of the first moving object 36 and the second moving object 6 is increased, so that the output power of the actuator 2 is further increased.

Furthermore, elastic forces are charged in respective spring members 13a, 13b and 13c corresponding to rotation motion of the second moving object 6 around the axis of the shaft 3. As a result, an angular region where the second moving object 6 is rotatable around the axis of the shaft 3 is restricted, so that rolling angle of the shaft 3 is decided.

By the way, in the above structure for restricting the rotation of the second moving object 6 by only the spring members 13a, 13b and 13c, there is a possibility that the second moving object 6 rotates over a permissible region when a force for rotating the second moving object 6 more than the permissible region around the axis of the shaft 3 from outside, so that it may affect driving characteristic of the actuator. Thus, a rotation restricting structure of the shaft 3 shown in FIG. 4 is provided for mechanically stopping the rotation of the second moving object 6 when a rotation force more than the permissible region is applied to the second moving object 6 around the axis of the shaft 3 from outside.

A rear end portion 3a of the shaft 3 is formed to have a substantially D-shaped section. On the other hand, a substantially sector shaped fitting hole 14 into which the rear end portion 3a of the shaft 3 is fitted thereby restricting the rotation of the shaft 3 around the axis is formed on the sealing member 72 in rear side. By fitting the rear end portion 3a of the shaft 3 into the fitting hole 14, rotation angle around the axis of the shaft 3 is restricted in a fixed region. Although tapered faces 31 are formed to be a angle section on the fitting hole 14, when the second moving object 6 is in a neutral position of amplitude, a flat face portion of substantially D-shaped section of the rear end portion 3a of the shaft 3 does not contact with the tapered faces 31 of angle section, so that the moving object 6 is reciprocally rotatable around the axis of the shaft 3. When the moving object 6 rotates over the permissible region around the axis of the shaft 3 in a direction shown by arrow R1, the flat face portion of substantially D-shaped section of the rear end portion 3a of the shaft 3 contacts with the tapered faces 31 of angle section, so that the rotation is restricted more. The same goes for the case for rotating in opposite direction shown by arrow R2. Thereby, the rotation of the second moving object 6 over the rolling angle is mechanically restricted, so that reliability of the actuator 2 against the externally applied load or impact load, and so on can be ensured.

In addition, the rear end portion 3a of the shaft 3 is used as a reference plane when the second yoke 5 is press-fitted to and fixed on the shaft 3, too. Specifically, by press-fitting the second yoke 5 in a manner so that a flat bottom face 25a of a rectangular cornered U-shaped groove 25 of the second yoke 5 (refer to FIG. 4) and the flat face portion of substantially D-shaped section of the rear end portion 3a of the shaft 3 become substantially parallel to each other, a proper assembling angle of the second yoke 5 with respect to the shaft 3 can easily be defined.

Furthermore, in the modified example shown in FIG. 5, it is possible that a plurality of (for example, four) engaging protrusions 26a is formed on an end face of the spring receiving member 26 which is not contact with the spring member 13a, 13b or 13c as shown in FIG. 6, and they are engaged with the gaps 43 formed on the first yoke 35. By such a configuration, the rotation of the spring receiving member 26 with respect to the first yoke 35 around the axis of the shaft 3 is restricted.

In addition, as shown in FIG. 7, since a plurality of protrusions 27 is provided on a face of the spring receiving member 26, when the protrusions 27 are inserted into end portions of the grooves 25 of the second yoke 5 in longitudinal direction, the spring receiving members 26 are fixed to the second yoke 5 nonrotatably.

Figure 9:
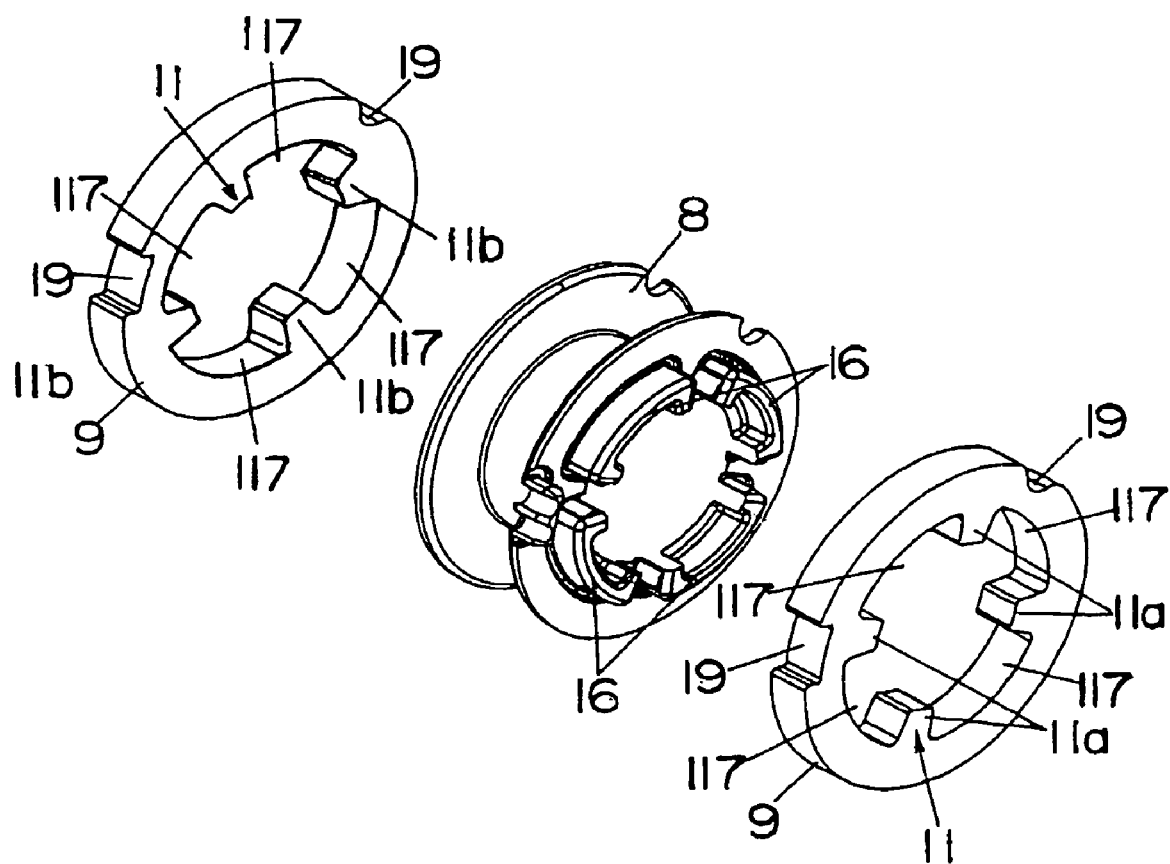
FIG. 9 is an exploded perspective view showing a configuration of a second bobbin and second stationary yokes which constitute the second stator of the above actuator.

As shown in FIG. 8B and FIG. 8C, a number of magnetic poles 11 less than a predetermined number (four positions in the figure) is provided on an inner periphery portion of each second stationary yoke 9 for facing poles of the second moving object 6 (the outer faces 4a of the second permanent magnets 4 and outer faces 5a of the yoke 5). As shown in FIG. 9, cuttings (SIC: correctly 117) 17 are respectively formed between adjoining two magnetic poles 11 of the second stationary yoke 9. In this way, by providing the cuttings (SIC) 17 between the magnetic poles 11, it is possible to reduce leakage of magnetic flux to the shaft 3 even when the shaft 3 is made of a magnetic material such as iron, so that the magnetic flux by the second permanent magnets 4 can be utilized effectively in the second stationary yokes 9 side. Beside, it is sufficient that the number of the magnetic poles 11 is more than at lest one, but it is possible to increase the number of the magnetic poles 11 to the same number as the number (four) of the permanent magnets 4.

In case of providing the second stationary yokes 9 on both sides of the second bobbin 8 in the axial direction of the shaft 3 shown in FIG. 8A, the second stationary yokes 9 are respectively disposed in a manner so that positions of the magnetic poles 11a of one second stationary yoke 9 are not coincided with positions of the magnetic poles 11b of the other second stationary yoke 9 around the axis of the shaft 3 of the second moving object 6, as shown in FIG. 8B and FIG. 8C. Furthermore, at the initial position of the second moving object 6 when no current is supplied to the second coil 7, each magnetic pole 11a of one second stationary yoke 9 is positioned to face a contact point 15a of an end portion of the second permanent magnet 4 and the second yoke 5 around the axis of the shaft 3, and each magnetic pole 11b of the other second stationary yoke 9 is positioned to face another contact point 15b of the other end portion of the same second permanent magnet 4 and the second yoke 5. Thereby, a gap of the magnetic pole 11a of one second stationary yoke 9 and a gap of the magnetic pole 11b of the other second stationary yoke 9 with respect to the same second permanent magnet 4 becomes substantially the same, so that the rolling driving of the second moving object 6 is effectively performed.

Furthermore, as shown in FIG. 9, stationary yoke positioning portions 16 for positioning the stationary yoke 9 with respect to the second bobbin 8 are respectively provided on both end faces of the second bobbin 8 in the axial direction of the shaft 3. In the example shown in FIG. 6 (SIC), the stationary yoke positioning portions 16 each which is a protruding rib having an arc shape are provided for protruding at four positions with a predetermined distance on the end faces of the second bobbin 8. On the other hand, the cuttings (SIC) 17 are formed between adjoining two magnetic poles 11 on the stationary second yoke 9, as mentioned before. By attaching two second stationary yokes 9 respectively on both end faces of the second bobbin 8 along the axial direction of the shaft 3 in a manner so that the stationary yoke positioning portions 16 are respectively fitted into the cuttings (SIC) 17 of the second stationary yokes 9, the relative positions of two second stationary yokes 9 around the axis of the shaft 3 are fixed.

Furthermore, as shown in FIG. 10A, a rotation restricting portion 20a, which is protruded toward an inner peripheral face side by, for example, press work, is formed on the substantially cylindrical shaped shielding case 12. Corresponding to this, engaging concave portions 19 which are to be engaged with the rotation restricting portion 20a, are formed on the outer peripheral faces of the second bobbin 8 and the second stationary yokes 9. By fitting the second stator 10 to the inner peripheral face of the shielding case 12 in a manner so that the engaging concave portions 19 are engaged with the rotation restricting portion 20a, the rotation of the second stationary yokes 9 with respect to the shielding case 12 around the axis of the shaft 3 is restricted, too. Similarly, a plurality of stoppers 20b protruding toward the inner peripheral face side by, for example, press work is formed on the shielding case 12. For example, in FIG. 10A, when the second stator 10 is going to be fitted to the inner peripheral face of the shielding case 12, for example, from an opening at right side of the shielding case 12, the second stationary yoke 9 at left side contacts the stoppers 20b, so that the movement in the axial direction of the shaft 3 is restricted at that position. According to such a configuration, fixing operation of the second stator 10 to the shielding case 12 becomes easier. Alternatively, by forming an engaging protruding portion on an outer peripheral face of each second stationary yoke 9 and forming a concave groove on the inner peripheral face of the shielding case 12 by punching of press work as the rotation restricting portion 20a, substantially the same effect can be obtained.

Furthermore, it is possible to provide a tubular or ring shaped magnetic shielding member 50 which is made of a nonmagnetic material between the reciprocal linear driving unit 2A and the rolling driving unit 2B as shown in FIG. 3. Thereby, although the reciprocal linear driving unit 2A and the rolling driving unit 2B are adjacently provided on a single common shaft 3 in axial direction thereof, magnetic fluxes from the reciprocal linear driving unit 2A and the rolling driving unit 2B can be shielded by the magnetic shielding member 50. Furthermore, by forming the magnetic shielding member 50 as tubular shape or ring shape, it is possible to shield the magnetic fluxes by the first permanent magnets 34 and the second permanent magnets 4 without leakage. As a result, it is possible to have no effect of magnetic force by the first permanent magnets 34 in the reciprocal linear driving unit 2A or the second permanent magnets 4 in the rolling driving unit 2B to the other of the rolling driving unit 2B or the reciprocal linear driving unit 2A, so that two motions of the reciprocal linear driving in the axial direction of the shaft 3 by the reciprocal liner driving unit 2A and the rolling driving around the axis of the shaft 3 by the rolling driving unit 2B can be obtained stably.

As mentioned above, according to the actuator 2 in accordance with this embodiment, the reciprocal liner driving unit 2A and the rolling driving unit 2B are respectively provided at different positions along the common single shaft 3 along the axial direction thereof, so that two motions of the reciprocal linear driving in axial direction and the rolling driving around the axis of the shaft 3 can be performed simultaneously.

Furthermore, the tubular shaped or ring shaped first permanent magnets 34 constituting the reciprocal linear driving unit 2A and the flat plate shaped second permanent magnets 4 constituting the rolling driving unit 2B are respectively provided on the first moving object 36 side and the second moving object 6 side instead of the first stator 40 side and the second stator 10 side. Therefore, in case of the tubular shaped or ring shaped first permanent magnet 34, an inside diameter and an outside diameter of the first permanent magnet 34 become smaller, and thereby a volume of the first permanent magnet 34 becomes smaller, in comparison with the case that the permanent magnet having a larger diameter is provided on an inner face of the shielding case like the conventional one. As a result, the reciprocal linear driving unit 2A can be miniaturized and light-weighted, and the cost of the first permanent magnet 34 in material can be reduced. Furthermore, since the first permanent magnet 34 can be manufactured by, for example, cutting a tubular shaped permanent magnet magnetized in axial direction thereof in round or magnetizing a ring shaped magnetic material in thickness direction thereof, so that the manufacture of the first permanent magnet 34 becomes easier, and the cost of the first permanent magnet 34 in manufacture can be reduced.

In case of the flat plate shaped second permanent magnet 4, a volume of the second permanent magnet 4 similarly becomes smaller in comparison with the case that the permanent magnet having a larger diameter is provided on an inner face of the shielding case like the conventional one. As a result, the rolling driving unit 2B can be miniaturized and light-weighted, and the cost of the second permanent magnet 4 in material can be reduced. Furthermore, since the second permanent magnet 4 is magnetized in thickness direction, it can be manufactured by cutting a larger plate shaped permanent magnet magnetized in thickness direction in rectangles, and thereby, the manufacture of the second permanent magnet 4 becomes easier and the cost of the second permanent magnet 4 in manufacture can be reduced. By synthesizing there effects, miniaturization and light-weighting and significant cost down of the actuator 2 can be realized.

Subsequently, a relationship between frequency and amplitude of the first moving object 36 or the second moving object 6 when a voltage of alternating current supplied to the first coil 37 or the second coil 7 is set to be constant, and a relationship between the frequency and current at that time in the actuator 2 in accordance with this embodiment are described with reference to a graph shown in FIG. 13.

Figure 13:
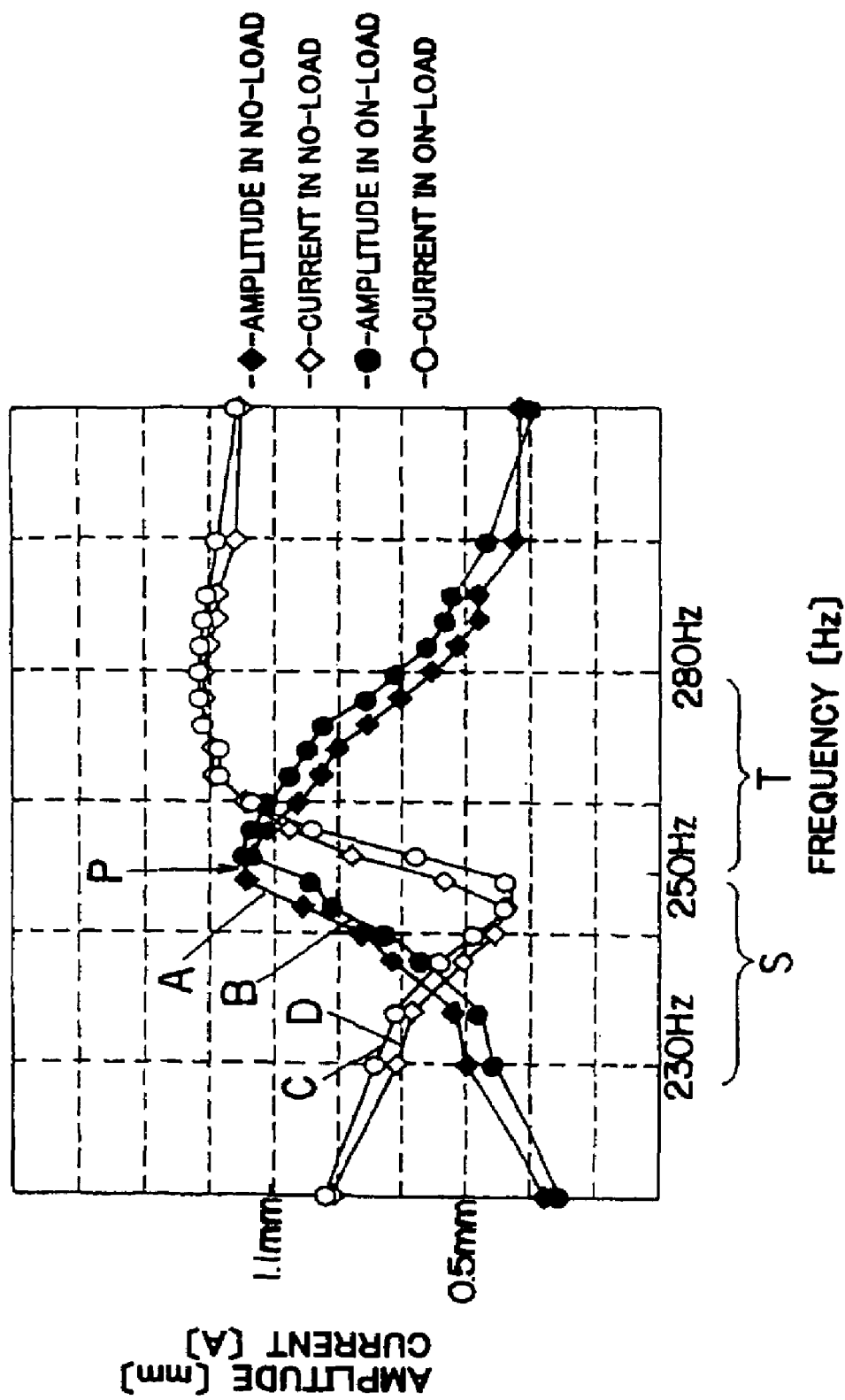
FIG. 13 is a graph showing a relation between frequency of alternating current and amplitude of the moving object when voltage is made to be constant in the actuator and a relation between the frequency and current at that time.

In FIG. 13, curves A and B respectively show the relationship between frequency and amplitude of the first moving object 36 or the second moving object 6 when the voltage is set to be constant, and curves C and D respectively show the relationship between the frequency and current. In FIG. 13, a mark ♦ designates amplitude in no-load, a mark ● designates amplitude in on-load, a mark ◇ designates current value in no-load, and a mark ○ designates current value in no-load, respectively.

As mentioned before, the oscillation quantity (amplitude quantity) of the first moving object 36 or the second moving object 6 can be increased by supplying the alternating current having a frequency near to the resonance vibration frequency (shown by point P in FIG. 13) defined by the spring constant of the spring members 13a, 13b and 13c and the mass of the first moving object 36 and the second moving object 6 to the first coil 37 or the second coil 7. For example, in the vicinity of frequency 250 Hz, the amplitude of the first moving object 36 or the second moving object 6 shows the maximum value 1.1 mm. In the region S of the frequency equal to or larger than 230 Hz and equal to or smaller than 250 Hz and in the region T equal to or larger than 250 Hz and equal to or smaller than 280 Hz, the amplitude shows a value equal to or larger than 0.5 mm, respectively.

When the frequency of the alternating current flowing to the first coil 37 or the second coil 7 is set in these regions, it is possible to enlarge the oscillation quantity (amplitude quantity) of the first moving object 36 or the second moving object 6 with utilizing the spring members 13a, 13b and 13c. Hereupon, in the vicinity of the resonance vibration frequency, and in a region of frequency higher than the resonance vibration frequency and in a region of frequency lower than the resonance vibration frequency, amplitude similar to this can be obtained. When the first moving object 36 is driven reciprocally and linearly or the second moving object 6 is driven rollingly by setting the frequency lower than the resonance vibration frequency (when the frequency is set in the region S), it is possible to perform the reciprocal linear driving with the aimed amplitude by small current. Especially, when a power supply of the actuator 2 is a battery, it is possible to make the operation life of the battery longer. On the other hand, when the frequency is set to be higher than the resonance vibration frequency (when the frequency is set in the region T), although the current becomes larger, it is possible to perform the reciprocal linear driving or the rolling driving with the aimed amplitude so as to take a large output power.

Since FIG. 13 merely shows an example, there may be a case that the resonance frequency of the reciprocal linear driving unit 2A and the resonance frequency of the rolling driving unit 2B are different each other. For example, it is possible that at least one of the reciprocal linear driving unit 2A and the rolling driving unit 2B is driven by a frequency near to but lower than the resonance frequency of the driving unit and the other is driven by a frequency near to but higher than the resonance frequency of the driving unit. Alternatively, it is possible that the reciprocal linear driving unit 2A and the rolling driving unit 2B are driven by a frequency near to but lower than the resonance frequency of these driving units. In reverse, it is possible that the reciprocal linear driving unit 2A and the rolling driving unit 2B are driven by a frequency near to but higher than the resonance frequency of these driving units. Furthermore, the frequency of the alternating current supplied to the first coil 37 of the reciprocal linear driving unit 2A and the frequency of the alternating current supplied to the second coil 7 of the rolling driving unit 2B may be the same as or different from each other.

The above-mentioned actuator 2 can be used as various kinds of driving force. As an example, a configuration of a power toothbrush comprising the above-mentioned actuator is shown in FIG. 14.

The power toothbrush 1 comprises a tubular shaped slender housing 22, the actuator 2 shown in above FIG. 1 provided in front side in the housing 22 in longitudinal direction, a battery (secondary battery) 21 provided in rear side in the housing 22 in the longitudinal direction, a control circuit 32, an electric switch 33 provided on an outer periphery portion of the housing 22, and so on. An end portion of the shaft 3 of the actuator 2 is protruded outward from a front end face of the housing 22.

Figure 14:
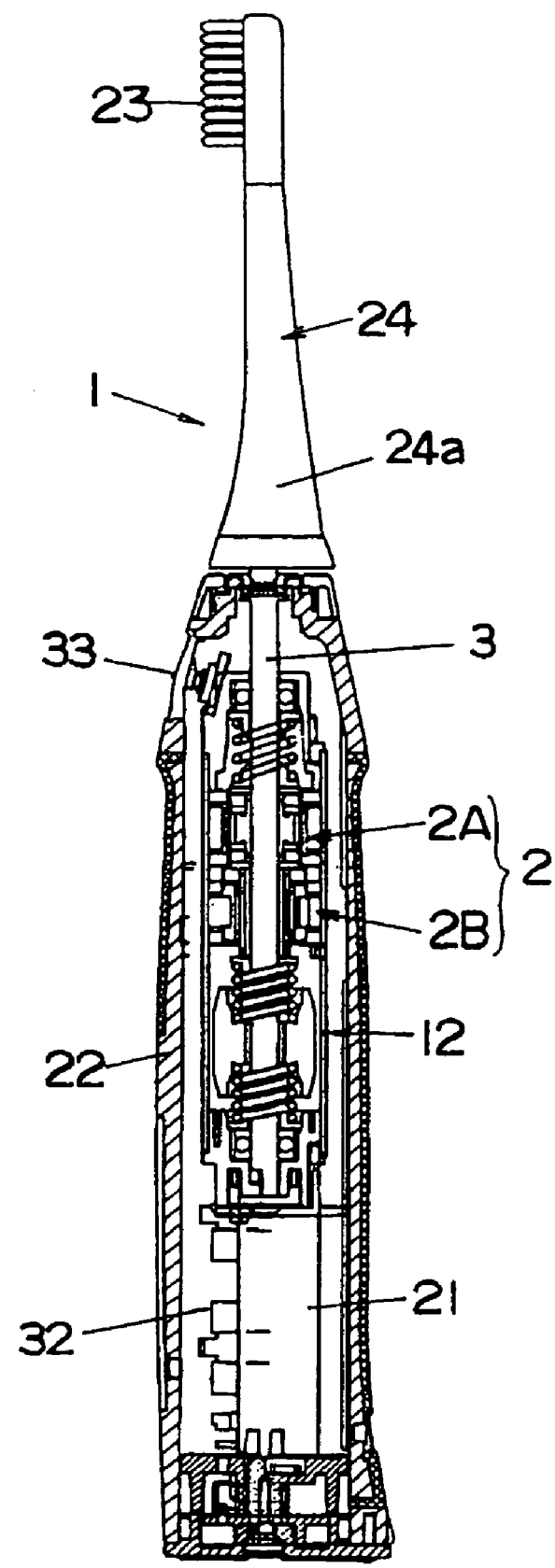
FIG. 14 is a sectional view showing a configuration of a power toothbrush using the actuator capable of reciprocal linear driving and rolling driving in accordance with an embodiment of the present invention.
Figure 15:
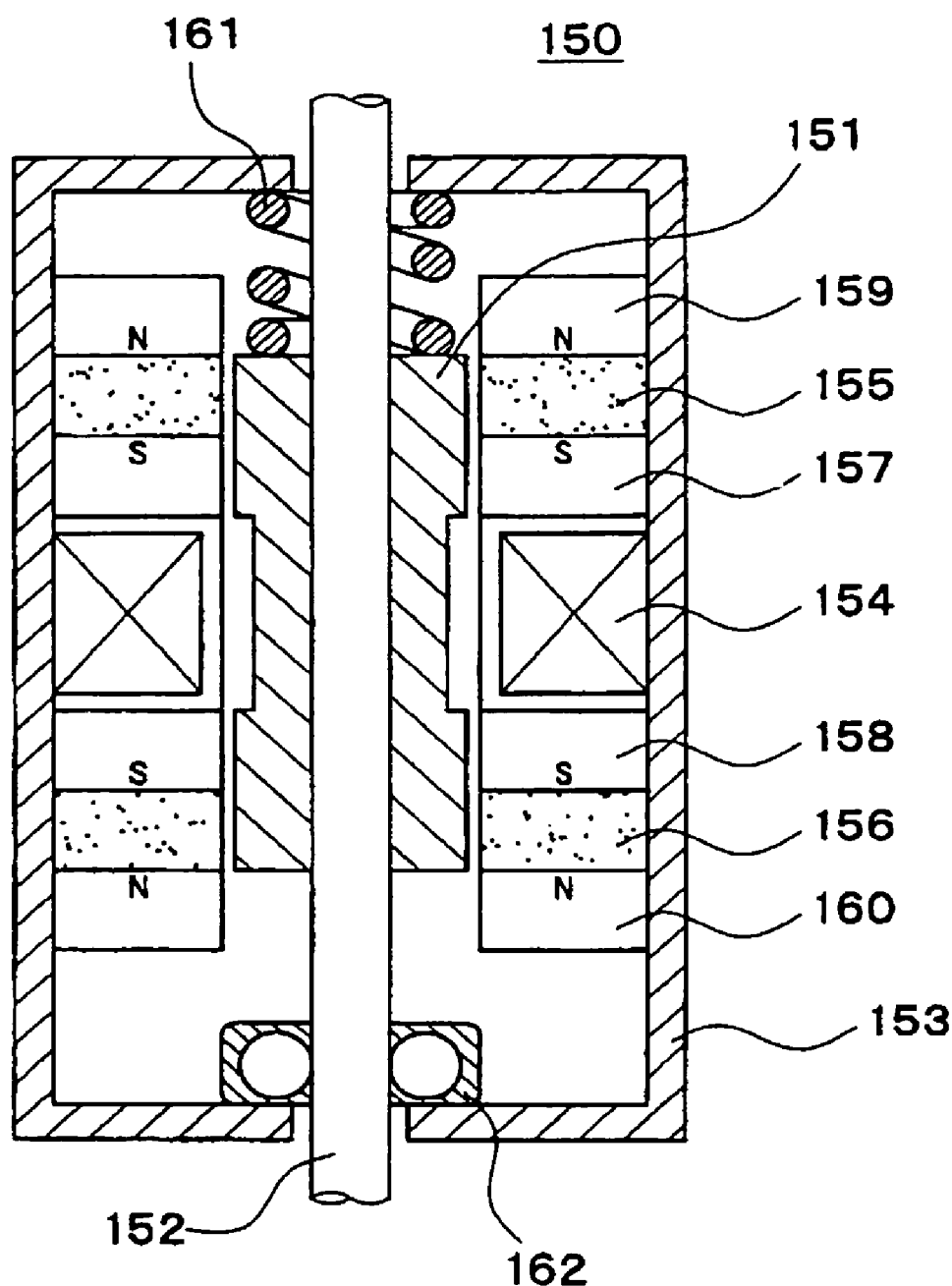
FIG. 15 is a sectional view showing a configuration of a conventional reciprocation type linear driving actuator (reference example).

In the example shown in FIG. 14, since a brush body 24 is a type that a brush portion 23 at a front end thereof is implanted in a direction substantially perpendicular to longitudinal direction of the brush body 24, it is attached on the shaft 3 in a manner so that a rear end portion of a handle portion 24a of the brush body 24 is detachably attached on an end of the shaft 3, and not rotatable around the axis of the shaft 3. As shown in FIG. 1 and FIG. 2 (SIC: correctly FIG. 2A), since a vicinity of the front end of the shaft 3 is formed to have a substantially D-shaped section, by forming a fitting hole having a substantially D-shaped section, which is to be fitted to the front end portion of the shaft 3, on the handle portion 24a of the brush body 24, it is possible to restrict the brush body 24 not to rotate around the axis of the shaft 3. As a result, a positional relationship between the protruding direction of the brush portion 23 of the brush body 24 and the electric switch 33 provided on the housing 22 can be made constant, so that operability as the power toothbrush may not be failed.

The control circuit 32 supplies the alternating current(s) to the first coil 37 of the reciprocal linear driving unit 2A and/or the second coil 7 of the rolling driving unit 2B corresponding to witching operation of the electric switch 33 by a user. Thereby, it is selectable among a mode for driving the shaft 3 reciprocally and linearly in the axial direction thereof, a mode for driving the shaft 3 rollingly around the axis thereof, and a mode for driving the shaft 3 reciprocally and linearly in the axial direction thereof and rollingly around the axis thereof simultaneously.

By operating the electric switch 33 of the power toothbrushes 1 configured as above so as to supply a current to the first coil 37 or the second coil 7 of the actuator 2, the shaft 3 can be driven in the reciprocal linear driving in the axial direction thereof or the rolling driving around the axis thereof. Thereby, the brush body 24 attached on the shaft 3 is performed the reciprocal linear driving in the axial direction or in the rolling driving around the axis, so that brushing of teeth can be performed by driving the brush portion 23 in the reciprocal linear driving or the rolling driving in user's preference.

As mentioned above, according to the actuator 2 in accordance with this embodiment, the first permanent magnets 34 of substantially ring shape or substantially tubular shape of the reciprocal linear driving unit 2A which drives the shaft 3 in axial direction thereof are fitted to and fixed on the shaft 3 directly or via the spacer 41, so that the inside diameter and the outside diameter of the first permanent magnets 34 become smaller, and the volume of each first permanent magnet 34 becomes smaller. Furthermore, it is configured that the second permanent magnets 4 of the rolling driving unit 2B which drives the shaft 3 reciprocally and rotatively in a predetermined region around the axis thereof are formed to be flat plate shape and fitted to the grooves 25 formed on the yoke 5 of the moving object 6, so that the volume of each second permanent magnet 4 becomes smaller, and manufacturing process of the permanent magnet 4 and assembling process of the moving object 6 are simplified. As a result, the costs of the actuator 2 and the power toothbrush 1 using the same can be reduced.

This application is based on Japanese patent application 2003-139573 filed in Japan, the contents of which are hereby incorporated by references of the specification and drawings of the above patent application.

Although the present invention has been fully described by way of example with reference to the accompanying drawings, it is to be understood that various changes and modifications will be apparent to those skilled in the art. Therefore, unless otherwise such changes and modifications depart from the scope of the present invention, they should be construed as being included therein.

INDUSTRIAL APPLICABILITY

As mentioned above, according to the present invention, in the actuator capable of reciprocal linear driving and rolling driving, the reciprocal linear driving unit and the rolling driving unit are adjacently provided on the common single shaft in the axial direction thereof, so that the reciprocal linear driving in the axial direction and the rolling driving around the axis can be performed by only one shaft. Furthermore, the permanent magnets constituting the reciprocal linear driving unit and the rolling driving unit are provided on the moving object side instead of the stator side, in other words they are provided around the axis of the shaft, so that the permanent magnets can be miniaturized and light-weighted, respectively, in comparison with the case that the permanent magnets of larger diameter are provided on the stator side like the conventional one. Following to this, it is possible to realize the miniaturization, light-weighting and cost reduction of the actuator much more.

Furthermore, according to the power toothbrush using the actuator capable of reciprocal linear driving and rolling driving in accordance with the present invention, it is possible to drive the brush body attached to the front end of the shaft in any one of the mode for performing the shaft in the reciprocal linear driving in the axial direction thereof, the mode for performing the shaft in the rolling driving around the axis thereof, and the mode for performing the shaft in the reciprocal linear driving in the axial direction thereof and in the rolling driving around the axis thereof simultaneously. Still furthermore, the miniaturization, light-weighting and cost reduction of the actuator itself can be realized as mentioned above, so that it is possible to realize the miniaturization, light-weighting and cost reduction of the power toothbrush using the same.

The invention claimed is:

1. An actuator capable of reciprocal linear driving and rolling driving comprising a reciprocal linear driving unit and a rolling driving unit which are arranged to adjoin in axial direction of a shaft;
   the shaft being pivoted to be enabled reciprocal linear driving in the axial direction thereof and pivoted to be enabled rolling driving around the axis of the shaft in a predetermined region;
   the reciprocal linear driving unit comprising: a first moving object having the shaft and first permanent magnets each magnetized so that polarities of both end portions in the axial direction of the shaft are different and fitted to and fixed on the shaft; and a first stator having a coil disposed to face end faces of the first permanent magnets parallel to the axial direction of the shaft with a predetermined clearance and generating magnetic field when current is supplied;
   the rolling driving unit comprising: a second moving object having the shaft, a second yoke fixed on the shaft and at least one second permanent magnet attached to adjoin the second yoke around the axis of the shaft; and a tubular shaped second stator having a second coil wound around the axis of the shaft to enclose the second moving object, and second stationary yokes disposed to face an outermost peripheral portion of the second yoke and the second permanent magnet with a predetermined clearance in a direction perpendicular to the axis of the shaft; and
   by supplying an alternating current to the first coil and/or the second coil, the first moving object being driven reciprocally and linearly in the axial direction of the shaft and/or the second moving object being driven rollingly around the axis of the shaft in a predetermined angle region.

2. The actuator capable of reciprocal linear driving and rolling driving described in claim 1 characterized by comprising a switching means for switching among a mode for driving only the first moving object reciprocally and linearly in the axial direction of the shaft, a mode for driving only the second moving object rollingly in the predetermined angle region around the axis of the shaft, and a mode for driving the first moving object reciprocally and linearly in the axial direction of the shaft and for driving the second moving object rollingly around the axis of the shaft simultaneously.

3. The actuator capable of reciprocal linear driving and rolling driving described in claim 1 characterized by that
   the first moving object has two first permanent magnets of tubular shape or ring shape disposed at a predetermined distance in axial direction of the shaft, a plurality of first yokes fitted to and fixed on the shaft so as to adjoin respective end faces of the two first permanent magnets in the axial direction of the shaft, and an iron core of substantially tubular shape fitted to the shaft so as to be parallel to the axial direction of the shaft between the two first permanent magnets;
   the two first permanent magnets are magnetized in thickness direction thereof so that polarities of both end faces of each in the axial direction of the shaft are different each other, and fixed on the shaft so that polarities of opposing faces of them becomes same each other; and
   the first stator further comprises a first bobbin around which the first coil is wound, and at least a first stationary yoke provided on any side of the first bobbin in the axial direction of the shaft.

4. The actuator capable of reciprocal linear driving and rolling driving described in claim 3 characterized by that a distance between the two first permanent magnets fitted to and fixed on the first moving object is made narrower than a distance between the two first stationary yokes of the first stator, and a center position between the two first stationary yokes substantially coincides with a center position of the two first permanent magnets in the axial direction in a state that the first moving object is not driven reciprocally and linearly.

5. The actuator capable of reciprocal linear driving and rolling driving described in claim 1 characterized by that
   the second permanent magnet is flat plate shape, and magnetized in thickness direction thereof; and
   the second yoke is a substantially tubular shaped body press-fitted to and fixed on the shaft, and has at least one groove on an outer peripheral face thereof, which is parallel to the axial direction of the shaft and to which the second permanent magnet is fitted.

6. The actuator capable of reciprocal linear driving and rolling driving described in claim 1 characterized by that the second moving object has a length in a region where the reciprocal linear driving can be performed in the axial direction of the shaft by which a clearance between the second permanent magnet and the second stationary yoke is held constant.

7. The actuator capable of reciprocal linear driving and rolling driving described in claim 1 characterized by that
   the first moving object and spring members supporting the first moving object in the axial direction of the shaft constitute a vibration system of the reciprocal linear driving;
   the second moving object and spring members supporting the second moving object around the axis of the shaft constitute a vibration system of the rolling driving; and the spring members of the vibration system of the reciprocal linear driving serve as the spring members of the vibration system of the rolling driving.

8. The actuator capable of reciprocal linear driving and rolling driving described in claim 7 characterized by that
   a common vibrational absorption spindle is provided in the vibration system of the reciprocal linear driving and in the vibration system of the rolling driving; and
   when the reciprocal linear driving by the first moving object and the rolling driving by the second moving object are simultaneously performed, the vibrational absorption spindle is driven reciprocally and linearly in the axial direction of the shaft in opposite phase to that of the first moving object, and driven rollingly around the axis of the shaft in opposite phase to that of the second moving object.

9. The actuator capable of reciprocal linear driving and rolling driving described in claim 7 characterized by that the spring members of the vibration system of the reciprocal linear driving and the spring members of the vibration system of the rolling driving are constituted by torsion and compression coil springs, and spring receiving members are further comprised so as to restrict rotation of arms at both ends of the coil springs around the axis of the shaft.

10. The actuator capable of reciprocal linear driving and rolling driving described in claim 9 characterized by that the spring receiving members include spring hook portions which are not movable with respect to the first stator and the second stator, and spring hook portions which move with the first moving object and the second moving object.

11. The actuator capable of reciprocal linear driving and rolling driving described in claim 1 characterized by that
    the first moving object and spring members supporting the first moving object in the axial direction of the shaft constitute a vibration system of the reciprocal linear driving;
    the second moving object and spring members supporting the second moving object around the axis of the shaft constitute a vibration system of the rolling driving; and
    the reciprocal linear driving unit and/or the rolling driving unit are/is driven by supplying an alternating current having a frequency equal to or near to a resonance frequency of the vibration system of the reciprocal linear driving to the first coil and/or supplying an alternating current having a frequency equal to or near to a resonance frequency of the vibration system of the rolling driving to the second coil.

12. The actuator capable of reciprocal linear driving and rolling driving described in claim 1 characterized by that a magnetic shielding member of tubular shape or ring shape which is made of a nonmagnetic material is provided between the reciprocal linear driving unit and the rolling driving unit in the axial direction of the shaft.

13. A power toothbrush using an actuator enabling reciprocal linear driving and rolling driving comprising: a brush body that brush is implanted at a front end thereof; an actuator which can perform reciprocal linear driving and rolling driving of the brush body in predetermined directions; an electric power supply for supplying electric power to the actuator; a driving circuit for supplying driving current to the actuator; and a control circuit for switching driving mode of the actuator corresponding to switching operation by a user, characterized by that
    the actuator comprises a reciprocal linear driving unit and a rolling driving unit which are arranged to adjoin in axial direction of a shaft;
    the shaft is pivoted to be enabled reciprocal linear driving in the axial direction thereof and pivoted to be enabled rolling driving around the axis of the shaft in a predetermined region;
    the reciprocal linear driving unit comprises: a first moving object having the shaft and first permanent magnets each magnetized so that polarities of both end portions in the axial direction of the shaft are different and fitted to and fixed on the shaft; and a first stator having a coil disposed to face end faces of the first permanent magnets parallel to the axial direction of the shaft with a predetermined clearance and generating magnetic field when current is supplied;
    the rolling driving unit comprises: a second moving object having the shaft, a second yoke fixed on the shaft and at least one second permanent magnet attached to adjoin the second yoke around the axis of the shaft; and a tubular shaped second stator having a second coil wound around the axis of the shaft to enclose the second moving object, and second stationary yokes disposed to face an outermost peripheral portion of the second yoke and the second permanent magnet with a predetermined clearance in a direction perpendicular to the axis of the shaft; and
    the control circuit switches among a mode for driving only the first moving object reciprocally and linearly in the axial direction of the shaft, a mode for driving only the second moving object rollingly around the axis of the shaft in a predetermined angle region, and a mode for driving the first moving object reciprocally and linearly in the axial direction of the shaft and driving the second moving object rollingly around the axis of the shaft in a predetermined angle region simultaneously, corresponding to switching operation by the user.

* * * * *